(12) United States Patent
Goto et al.

(10) Patent No.: US 10,975,296 B2
(45) Date of Patent: Apr. 13, 2021

(54) ELECTROCHROMIC COMPOUND, ELECTROCHROMIC COMPOSITION, AND ELECTROCHROMIC ELEMENT

(71) Applicants: Daisuke Goto, Kanagawa (JP); Toshiya Sagisaka, Kanagawa (JP); Satoshi Yamamoto, Kanagawa (JP); Masato Shinoda, Kanagawa (JP); Mamiko Inoue, Kanagawa (JP)

(72) Inventors: Daisuke Goto, Kanagawa (JP); Toshiya Sagisaka, Kanagawa (JP); Satoshi Yamamoto, Kanagawa (JP); Masato Shinoda, Kanagawa (JP); Mamiko Inoue, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 15/860,698

(22) Filed: Jan. 3, 2018

(65) Prior Publication Data

US 2018/0208834 A1 Jul. 26, 2018

(30) Foreign Application Priority Data

Jan. 26, 2017 (JP) .............................. JP2017-012438

(51) Int. Cl.
| | | |
|---|---|---|
| *C09K 9/02* | (2006.01) | |
| *C07C 217/92* | (2006.01) | |
| *C07D 307/91* | (2006.01) | |
| *C07D 333/76* | (2006.01) | |
| *C07D 209/86* | (2006.01) | |
| *C07D 307/77* | (2006.01) | |
| *C08F 122/22* | (2006.01) | |
| *C08F 120/36* | (2006.01) | |
| *C08F 120/38* | (2006.01) | |
| *G02F 1/153* | (2006.01) | |

(Continued)

(52) U.S. Cl.
CPC .............. *C09K 9/02* (2013.01); *C07C 217/92* (2013.01); *C07D 209/86* (2013.01); *C07D 307/77* (2013.01); *C07D 307/91* (2013.01); *C07D 333/76* (2013.01); *C08F 120/36* (2013.01); *C08F 120/38* (2013.01); *C08F 122/1006* (2020.02); *C08F 122/22* (2013.01); *G02F 1/153* (2013.01); *G02F 1/15165* (2019.01); *C07C 2603/12* (2017.05); *C07C 2603/18* (2017.05); *C07C 2603/24* (2017.05); *C07C 2603/26* (2017.05); *C07C 2603/40* (2017.05); *C07C 2603/42* (2017.05); *C07C 2603/48* (2017.05); *C07C 2603/52* (2017.05); *C09K 2211/1007* (2013.01); *C09K 2211/1011* (2013.01); *C09K 2211/1018* (2013.01)

(58) Field of Classification Search
CPC ... G02F 2001/1515; G02F 1/153; C07K 9/02; C07D 209/86; C07D 307/77; C07D 307/91; C07D 333/76; C08F 120/36; C08F 120/38; C08F 122/105; C08F 122/22; C07C 217/92
See application file for complete search history.

(56) References Cited

U.S. PATENT DOCUMENTS

| | | |
|---|---|---|
| 2007/0228941 A1 | 10/2007 | Abe et al. |
| 2016/0005375 A1 | 1/2016 | Naijo et al. |

(Continued)

FOREIGN PATENT DOCUMENTS

| | | |
|---|---|---|
| JP | 62-156172 | 7/1987 |
| JP | 62-290768 | 12/1987 |

(Continued)

OTHER PUBLICATIONS

English abstract for KR2011034981A (published Apr. 6, 2011), pp. 1-11 (Year: 2011).*

(Continued)

*Primary Examiner* — Kristin A Vajda
(74) *Attorney, Agent, or Firm* — Oblon, McClelland, Maier & Neustadt, L.L.P.

(57) ABSTRACT

An electrochromic compound represented by the following formula (1) is provided:

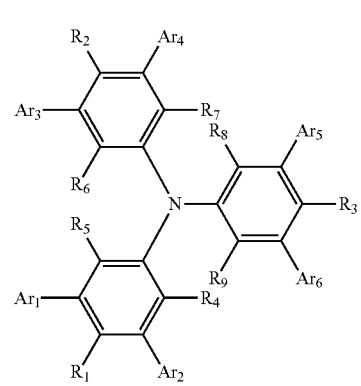

Formula (1)

where each of $R_1$ to $R_9$ and $Ar_1$ to $Ar_6$ independently represents one of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group; and at least one of $Ar_1$ to $Ar_6$ represents an aryl group, a heteroaryl group, a group in which two or more aryl and/or heteroaryl groups are bound to each other via a covalent bond, or a group in which at least two aryl or heteroaryl groups are condensed with each other to form a ring.

25 Claims, 2 Drawing Sheets

(51) Int. Cl.
   *G02F 1/1516*   (2019.01)
   *C08F 122/10*   (2006.01)

(56) References Cited

U.S. PATENT DOCUMENTS

| | | |
|---|---|---|
| 2016/0108072 A1 | 4/2016 | Inoue et al. |
| 2017/0010514 A1 | 1/2017 | Yashiro et al. |
| 2017/0168366 A1 | 6/2017 | Shinoda et al. |
| 2017/0226413 A1 | 8/2017 | Goto et al. |
| 2017/0235203 A1 | 8/2017 | Yamamoto et al. |
| 2017/0329199 A1 | 11/2017 | Yashiro et al. |
| 2017/0336691 A1 | 11/2017 | Yamamoto et al. |

FOREIGN PATENT DOCUMENTS

| | | | | |
|---|---|---|---|---|
| JP | 02178669 A | * | 7/1990 | |
| JP | 2002-175883 | | 6/2002 | |
| JP | 2007-291064 | | 11/2007 | |
| JP | 2011-506626 | | 3/2011 | |
| JP | 2012-062450 | | 3/2012 | |
| JP | 2016-038572 | | 3/2016 | |
| KR | 2011034981 A | * | 4/2011 | ............ C09K 11/06 |
| KR | 10-1072817 | | 10/2011 | |
| KR | 10-2011-0123701 | | 11/2011 | |
| KR | 10-2015-0116337 | | 10/2015 | |
| KR | 10-2016-0013692 | | 2/2016 | |
| KR | 10-2016-0113783 | | 10/2016 | |
| WO | WO2009/067419 A1 | | 5/2009 | |
| WO | WO2014/021572 | | 2/2014 | |
| WO | WO2014/073791 | | 5/2014 | |
| WO | WO2014/200260 | | 12/2014 | |
| WO | WO2015/041492 | | 3/2015 | |
| WO | WO2015/130069 | | 9/2015 | |
| WO | WO2015/194791 | | 12/2015 | |
| WO | WO2016/104289 | | 6/2016 | |
| WO | WO-2016091887 A2 | * | 6/2016 | ........... H01L 51/006 |
| WO | WO2016/111254 | | 7/2016 | |
| WO | WO2016/148425 | | 9/2016 | |
| WO | WO2016/167491 | | 10/2016 | |

OTHER PUBLICATIONS

Office Action in corresponding Japanese Patent Application No. 2017-012438 dated Dec. 1, 2020.

* cited by examiner

ELECTROCHROMIC COMPOUND, ELECTROCHROMIC COMPOSITION, AND ELECTROCHROMIC ELEMENT

CROSS-REFERENCE TO RELATED APPLICATIONS

This patent application is based on and claims priority pursuant to 35 U.S.C. § 119(a) to Japanese Patent Application No. 2017-012438, filed on Jan. 26, 2017, in the Japan Patent Office, the entire disclosure of which is hereby incorporated by reference herein.

BACKGROUND

Technical Field

The present disclosure relates to an electrochromic compound, an electrochromic composition, and an electrochromic element.

Description of the Related Art

Electrochromic elements utilizing coloring and bleaching phenomena of electrochromic materials (electrochromic compounds) that cause electrochromism are actively researched and developed lately for application to display devices such as electronic paper and light shielder.

An electrochromic element generally includes a pair of electrodes and an electrolyte layer and an electrochromic layer both disposed between the electrodes. As a forward voltage or reverse voltage is applied to the electrochromic element, the electrochromic compound is colored or bleached.

The electrochromic element is, in principle, capable of reversibly switching between a colorless state and a colored state. The electrochromic element may include multiple color-developing layers that may respectively develop cyan, magenta, yellow, etc., to develop various colors. Thus, electrochromic elements are expected as multicolor display elements. To apply electrochromic elements to transparent display devices or multicolor display devices, electrochromic compounds need to be colorless and transparent in a bleached state.

SUMMARY

In accordance with some embodiments of the present invention, an electrochromic compound is provided. The electrochromic compound is represented by the following formula (1):

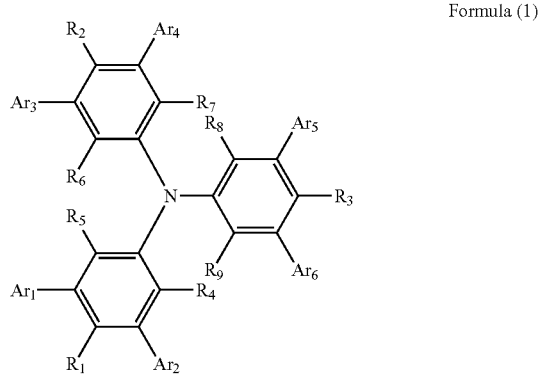

Formula (1)

where each of $R_1$ to $R_9$ independently represents one of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

each of $Ar_1$ to $Ar_6$ independently represents one of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group; and at least one of $Ar_1$ to $Ar_6$ represents an aryl group, a heteroaryl group, a group in which two or more aryl and/or heteroaryl groups are bound to each other via a covalent bond, or a group in which at least two aryl or heteroaryl groups are condensed with each other to form a ring.

In accordance with some embodiments of the present invention, an electrochromic composition is provided. The electrochromic composition includes the above electrochromic compound and a radical polymerizable compound.

In accordance with some embodiments of the present invention, an electrochromic element is provided. The electrochromic element includes a first electrode, an electrochromic layer on the first electrode, a second electrode facing the first electrode with a gap therebetween, and an electrolyte layer disposed between the first electrode and the second electrode. The electrochromic layer contains the above electrochromic compound.

In accordance with some embodiments of the present invention, an electrochromic element is provided. The electrochromic element includes a first electrode, a second electrode facing the first electrode with a gap therebetween, and an electrolyte layer disposed between the first electrode and the second electrode. The electrolyte layer contains the above electrochromic compound.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

Figure 1:
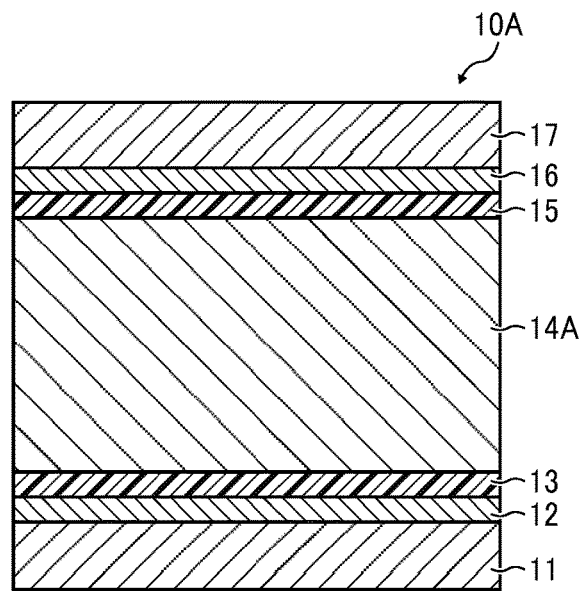
FIG. 1 is a schematic cross-sectional view of an electrochromic element in accordance with a first embodiment of the present invention.

The accompanying drawings are intended to depict example embodiments of the present invention and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Embodiments of the present invention are described in detail below with reference to accompanying drawings. In describing embodiments illustrated in the drawings, specific terminology is employed for the sake of clarity. However, the disclosure of this patent specification is not intended to be limited to the specific terminology so selected, and it is to be understood that each specific element includes all technical equivalents that have a similar function, operate in a similar manner, and achieve a similar result.

For the sake of simplicity, the same reference number will be given to identical constituent elements such as parts and materials having the same functions and redundant descriptions thereof omitted unless otherwise stated.

In accordance with some embodiments of the present invention, an electrochromic compound having excellent repetition durability and light durability is provided.

Electrochromic Compound

The electrochromic compound in accordance with some embodiments of the present invention is a radical polymerizable compound having a triarylamine backbone, represented by the following formula (1).

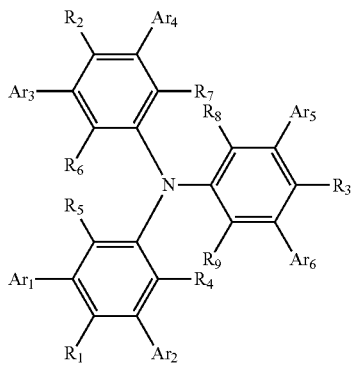

Formula (1)

In the formula (1), each of $R_1$ to $R_9$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group; each of $Ar_1$ to $Ar_6$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group; and at least one of $Ar_1$ to $Ar_6$ represents an aryl group, a heteroaryl group, a group in which two or more aryl and/or heteroaryl groups are bound to each other via a covalent bond, or a group in which two or more aryl and/or heteroaryl groups are condensed with each other to form a ring.

Specific examples of the halogen atom include, but are not limited to, fluorine, chlorine, bromine, and iodine.

Specific examples of the monovalent organic group include, but are not limited to, hydroxyl group, nitro group, cyano group, carboxyl group, carbonyl group, amide group, aminocarbonyl group, sulfonate group, sulfonyl group, sulfonamide group, aminosulfonyl group, amino group, alkyl group, alkenyl group, alkynyl group, aryl group, alkoxy group, aryloxy group, alkylthio group, arylthio group, and heteroaryl group. Each of these groups may have a substituent.

Specific examples of the monovalent organic group having a substituent include, but are not limited to: substituted carbonyl groups such as alkoxycarbonyl group, aryloxycarbonyl group, alkylcarbonyl group, arylcarbonyl group, monoalkylaminocarbonyl group, dialkylaminocarbonyl group, monoarylaminocarbonyl group, and diarylaminocarbonyl group; substituted sulfonyl groups such as alkoxysulfonyl group, aryloxysulfonyl group, alkylsulfonyl group, arylsulfonyl group, sulfoneamide group, monoalkylaminosulfonyl group, dialkylaminosulfonyl group, monoarylaminosulfonyl group, and diarylaminosulfonyl group; and substituted amino groups such as monoalkylamino group and dialkylamino group.

Among the above substituents, alkyl groups having 1 or more carbon atoms, alkenyl groups having 2 or more carbon atoms, alkynyl groups having 2 or more carbon atoms, aryl groups having 6 or more carbon atoms, heteroaryl groups having 2 or more carbon atoms, alkoxy groups, aryloxy groups, and heteroaryloxy groups are preferable.

Preferred examples of the alkyl groups having 1 or more carbon atoms include, but are not limited to, straight-chain, branched-chain, or cyclic alkyl groups having 1 to 30 carbon atoms, more preferably 1 to 18 carbon atoms, because their raw materials are easily available.

Specific examples of the alkyl groups having 1 or more carbon atoms include, but are not limited to, methyl group, ethyl group, propyl group, butyl group, tert-butyl group, isopropyl group, isobutyl group, pentyl group, hexyl group, heptyl group, ethylhexyl group, octyl group, decyl group, dodecyl group, 2-butyloctyl group, octadecyl group, cyclopropyl group, cyclobutyl group, cyclopentyl group, cyclohexyl group, and adamantyl group.

Preferred examples of the alkenyl groups having 2 or more carbon atoms include, but are not limited to, straight-chain, branched-chain, or cyclic alkenyl groups having 2 to 30 carbon atoms, more preferably 2 to 18 carbon atoms.

An alkenyl group having 2 or more carbon atoms is a group obtained by removing arbitrary two hydrogen atoms from an alkyl group having 1 or more carbon atoms. Specific examples of the alkenyl groups having 2 or more carbon atoms include, but are not limited to, vinyl group (ethenyl group), propenyl group, butenyl group, pentenyl group, hexenyl group, heptanyl group, octenyl group, decenyl group, dodecenyl group, octadecenyl group, cyclobutenyl group, cyclopentenyl group, and cyclohexenyl group.

Preferred examples of the alkynyl groups having 2 or more carbon atoms include, but are not limited to, straight-chain, branched-chain, or cyclic alkynyl groups having 2 to 30 carbon atoms, more preferably 2 to 18 carbon atoms.

An alkynyl group having 2 or more carbon atoms is a group obtained by removing arbitrary four hydrogen atoms from an alkyl group having 1 or more carbon atoms. Specific examples of the alkynyl groups having 2 or more carbon atoms include, but are not limited to, ethynyl group, propynyl group, butynyl group, pentynyl group, hexynyl group, heptynyl group, octynyl group, decynyl group, dodecynyl group, and octadecynyl group.

Specific examples of the aryl groups having 6 or more carbon atoms include, but are not limited to, phenyl group, o-tolyl group, m-tolyl group, p-tolyl group, p-chlorophenyl group, p-fluorophenyl group, p-trifluorophenyl group, naphthyl group, biphenyl group, anthryl group, phenanthryl group, pyrenyl group, fluorenyl group, benzopyrenyl group, and chrysenyl group.

Preferred examples of the heteroaryl groups having 2 or more carbon atoms include, but are not limited to, heteroaryl groups having 2 to 12 carbon atoms.

The heteroaryl group having 2 or more carbon atoms may comprise nitrogen atom, sulfur atom, oxygen atom, silicon atom, and/or selenium atom. Preferably, the heteroaryl group having 2 or more carbon atoms comprises at least one of nitrogen atom, sulfur atom, and oxygen atom.

Examples of the heteroaryl groups having 2 or more carbon atoms further include monocyclic heteroaryl groups and polycyclic heteroaryl groups.

Specific examples of the monocyclic heteroaryl groups include, but are not limited to, pyridine ring, pyrimidine ring, pyridazine ring, pyrazine ring, tetrazine, thiophene ring, furan ring, pyrrole, imidazole, pyrazole, thiazole ring, oxazole ring, isoxazole, oxadiazole ring, triazine ring, tetrazole ring, and triazole ring.

Specific examples of the polycyclic heteroaryl groups include, but are not limited to, quinoline group, isoquinoline group, quinazoline group, phthalazine group, indole group, benzothiophene group, benzofuran group, benzimidazole group, benzothiodiazole group, acridine group, phenoxazine group, phenothiazine group, carbazole group, benzodithiophene group, benzodifuran group, dibenzofuran group, and dibenzothiophene group.

Specific examples of the group in which two or more aryl and/or heteroaryl groups are bound to each other via a covalent bond and the group in which two or more aryl and/or heteroaryl groups are condensed with each other to form a ring include, but are not limited to, biphenyl group, terphenyl group, 1-phenylnaphthalene group, and 2-phenylnaphthalene group.

The polymerizable functional group refers to a polymerizable group having a carbon-carbon double bond. Examples of the polymerizable functional group include, but are not limited to, 1-substituted ethylene functional groups and 1,1-substituted ethylene functional groups.

Specific examples of the 1-substituted ethylene functional groups include, but are not limited to, a functional group represented by the following formula (i).

     Formula (i)

In the formula (i), $X_1$ represents an arylene group, an alkenylene group, —CO— group, —COO— group, or —CON($R_{100}$)— group (where $R_{100}$ represents a hydrogen atom, an alkyl group, an aralkyl group, or an aryl group), or —S— group. The arylene group and alkenylene group each may have a substituent.

Specific examples of the arylene group include, but are not limited to, phenylene group and naphthylene group. The phenylene group may have a substituent.

Specific examples of the alkenylene group include, but are not limited to, ethenylene group, propenylene group, and butenylene group.

Specific examples of the alkyl group include, but are not limited to, methyl group and ethyl group.

Specific examples of the aralkyl group include, but are not limited to, benzyl group, naphthylmethyl group, and phenethyl group.

Specific examples of the aryl group include, but are not limited to, phenyl group and naphthyl group.

Specific examples of the polymerizable functional group represented by the formula (i) include, but are not limited to, vinyl group, styryl group, 2-methyl-1,3-butadienyl group, vinyl carbonyl group, acryloyloxy group, acryloylamide group, and vinyl thioether group.

Specific examples of the 1,1-substituted ethylene functional groups include, but are not limited to, a functional group represented by the following formula (ii).

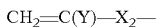     Formula (ii)

In the formula (ii), Y represents an alkyl group, an aralkyl group, an aryl group, a halogen atom, cyano group, nitro group, an alkoxy group, or —$COOR_{101}$ group (where $R_{101}$ represents a hydrogen atom, an alkyl group, an aralkyl group, an aryl group, or $CONR_{102}R_{103}$ (where each of $R_{102}$ and $R_{103}$ independently represents a hydrogen atom, an alkyl group, an aralkyl group, or an aryl group)). Each of these groups may have a substituent. $X_2$ represents a substituent, such as those exemplified for $X_1$ in the formula (i), a single bond, or an alkylene group. At least one of Y and $X_2$ represents oxycarbonyl group, cyano group, an alkenylene group, or an aromatic ring.

Specific examples of the alkyl group include, but are not limited to, methyl group and ethyl group. Specific examples of the aralkyl group include, but are not limited to, benzyl group, naphthylmethyl group, and phenethyl group. Specific examples of the aryl group include, but are not limited to, phenyl group and naphthyl group. Specific examples of the alkoxy group include, but are not limited to, methoxy group and ethoxy group.

Specific examples of the polymerizable functional group represented by the formula (ii) include, but are not limited to, α-acryloyloxy chloride group, methacryloyloxy group, α-cyanoethylene group, α-cyanoacryloyloxy group, α-cyanophenylene group, and methacryloyl amino group.

$X_1$, $X_2$, and Y each may have a substituent, such as a halogen atom, nitro group, cyano group, an alkyl group (e.g., methyl group and ethyl group), an alkoxy group (e.g., methoxy group and ethoxy group), an aryloxy group (e.g., phenoxy group), an aryl group (e.g., phenyl group and naphthyl group), and an aralkyl group (e.g., benzyl group and phenethyl group).

In particular, acryloyloxy group and methacryloyloxy group are preferred as the polymerizable functional group.

For improving resistance to redox, the polymerizable functional group is preferably substituted at the terminal of an alkyl group having 1 or more carbon atoms, an aryl group having 6 or more carbon atoms, or an alkyl-substituted aryl group having 7 or more carbon atoms; and more preferably at the terminal of an alkyl group.

Preferably, the polymerizable functional group is bound to the main backbone of the electrochromic compound via at least an alkyl group having 2 or more carbon atoms.

More preferably, the monovalent organic group having a substituent selected from a halogen atom, an alkyl group having 1 or more carbon atoms, an alkenyl group having 2 or more carbon atoms, an alkynyl group having 2 or more carbon atoms, an aryl group having 6 or more carbon atoms, a heteroaryl groups having 2 or more carbon atoms, an alkoxy group, an aryloxy group, and a heteroaryloxy group is bound to the main backbone of the electrochromic compound.

In a case in which the electrochromic compound is to be polymerized into a polymerized film, it is preferable that at least one of $R_1$ to $R_9$ is a polymerizable functional group so as to impart polymerizability to the electrochromic compound.

For preventing color change and suppressing a side reaction between molecules at the time when color is developed, preferably, each of $R_1$ to $R_9$ independently represents an alkyl group, an alkoxy group, or a polymerizable functional group.

More preferably, each of $R_1$ to $R_3$ independently represents an alkyl group, an alkenyl group, an alkynyl group, or an alkoxy group. This is because the para position of the nitrogen atom in triphenylamine has high electron density and reaction activity and is preferably substituted with such a substituent.

The group in which two or more aryl and/or heteroaryl groups are bound to each other via a covalent bond and the group in which two or more aryl and/or heteroaryl groups are condensed with each other to form a ring each contain 1 to 100 carbon atoms and may further contain a hetero atom. Preferably, the upper limit of the number of carbon atoms is 50, more preferably 36. Specific examples of the hetero atom include, but are not limited to, oxygen atom, sulfur atom, and nitrogen atom.

Preferably, the group in which two or more aryl and/or heteroaryl groups are bound to each other via a covalent bond and the group in which two or more aryl and/or heteroaryl groups are condensed with each other to form a ring each represent a group obtained by removing a hydrogen atom from an arbitrary carbon atom on an outer edge of a molecule of one of the following compounds. This is because the group in which two or more aryl and/or heteroaryl groups are bound to each other via a covalent bond and the group in which two or more aryl and/or heteroaryl groups are condensed with each other to form a ring each have a triplet energy relatively smaller than that of triphenylamine monomer (e.g., 3.0 eV).

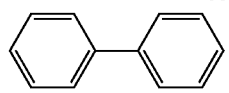

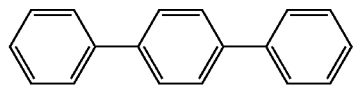

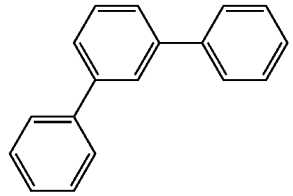
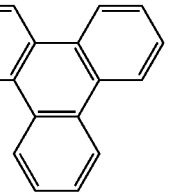

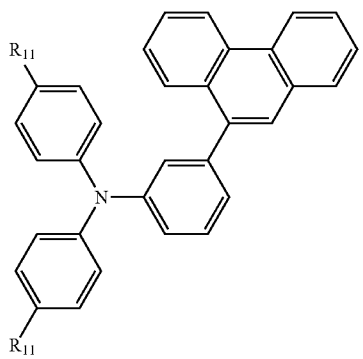

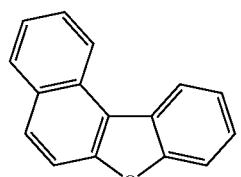

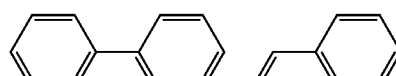

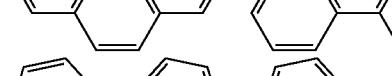

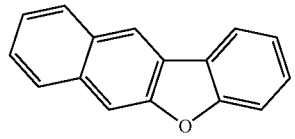

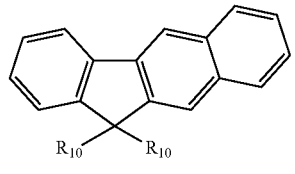

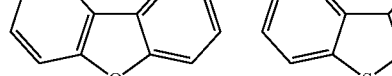
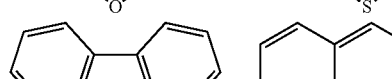

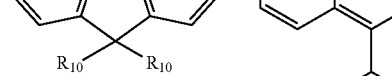

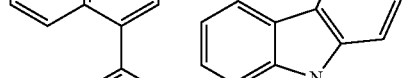

In the above formulae, each of $R_{10}$ and $R_{12}$ independently represents an alkyl group or an aryl group and $R_{11}$ represents an alkyl group, an alkenyl group, or an alkoxy group.

For transparency of the electrochromic compound in a bleached state, the group in which at least two aryl or heteroaryl groups are bound to each other via a covalent bond and the group in which at least two aryl or heteroaryl groups are condensed with each preferably has an absorption end at 400 nm or less, more preferably 380 nm or less.

Preferably, the group in which two or more aryl and/or heteroaryl groups are bound to each other via a covalent bond or the group in which two or more aryl and/or heteroaryl groups are condensed with each other to form a ring is introduced to the meta position of the nitrogen atom in a benzene ring constituting triphenylamine. In this case, steric hindrance or extension of conjugation does not occur much, thus improving light durability of the material itself without changing the color tone. On the other hand, when the group is introduced to the ortho position, the triphenylamine ring may be twisted due to steric hindrance of the group in which two or more aryl and/or heteroaryl groups are bound to each other via a covalent bond or the group in which two or more aryl and/or heteroaryl groups are condensed with each other to form a ring, thereby significantly increasing the oxidation potential. When the group is introduced to the para position, conjugation is extended. In many cases, the color of the electrochromic compound is changed from blue, derived from triphenylamine, to anther color.

The number of the group in which two or more aryl and/or heteroaryl groups are bound to each other via a covalent bond and the group in which two or more aryl and/or heteroaryl groups are condensed with each other to form a ring in the compound represented by the formula (1) can be selected from 1 to 6. Preferably, the number of the groups is from 1 to 3, and more preferably from 1 to 2. This is because a significant increase in number of the group in which two or more aryl and/or heteroaryl groups are bound to each other via a covalent bond and the group in which two or more aryl and/or heteroaryl groups are condensed with each other to form a ring, each of which does not contribute to color development, is not preferable in terms of color developing efficiency and material cost, compared to that of triphenylamine being chromophore.

Specific examples of the compound represented by the formula (1) include, but are not limited to, the following Examples Compounds. In the following chemical formulae, MeO— represents methoxy group.

Example Compound 1

Example Compound 2

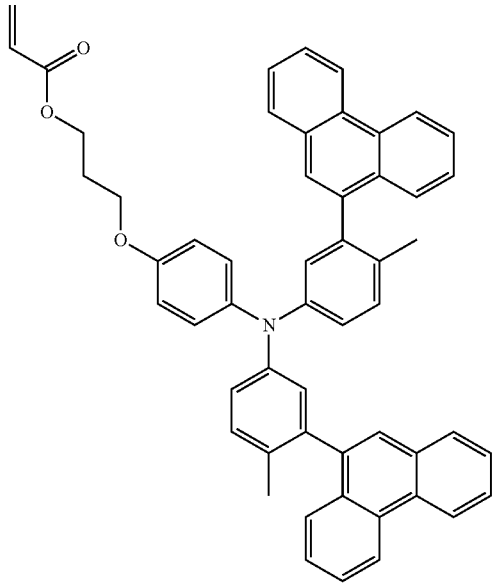

Example Compound 3

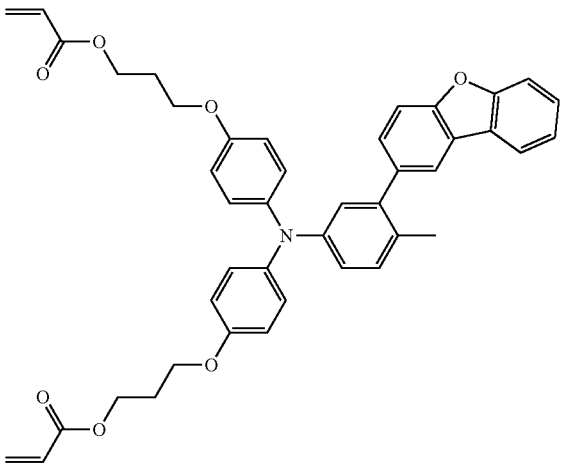

Example Compound 4

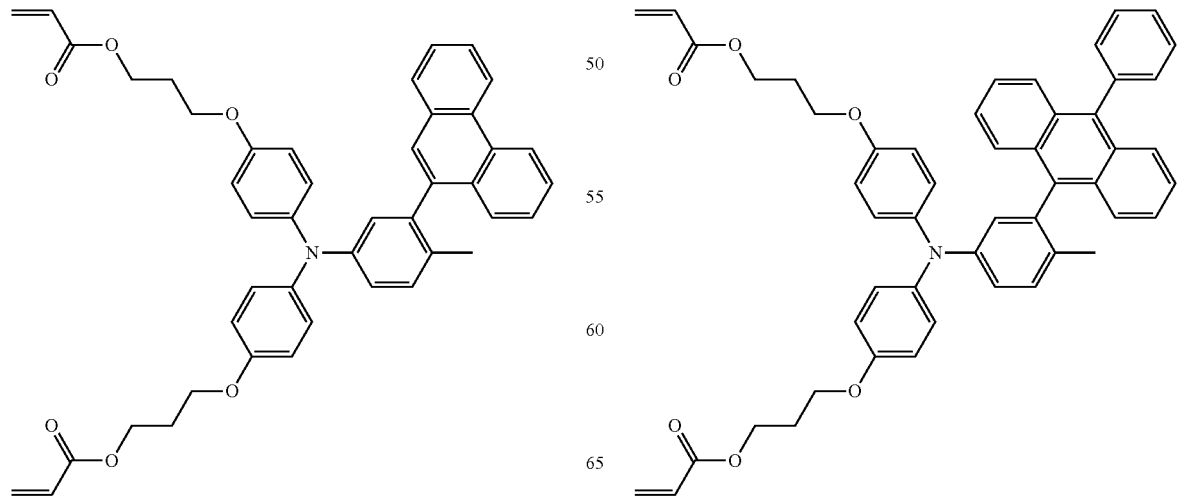

Example Compound 5
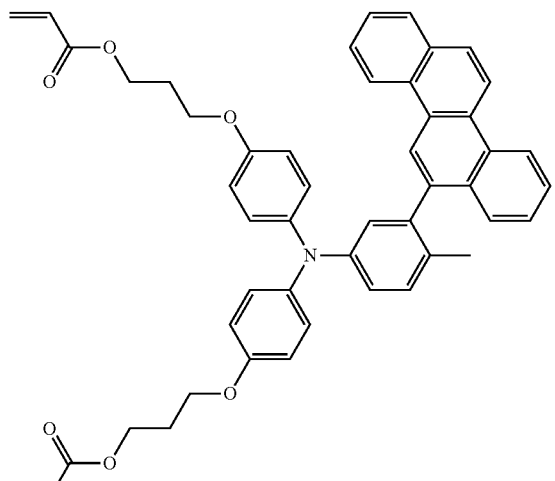
Example Compound 6
Example Compound 7
Example Compound 8
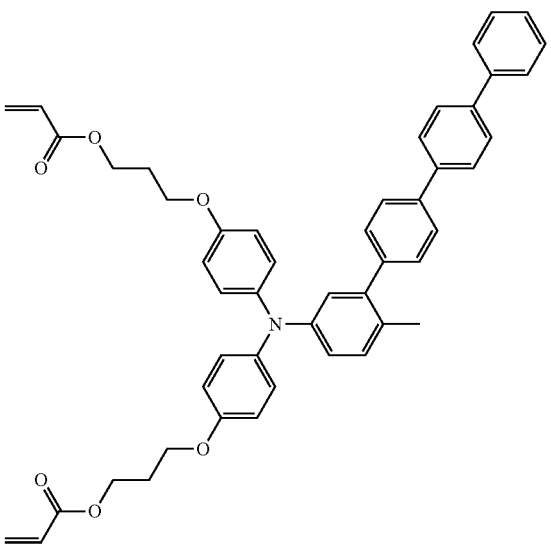
Example Compound 9
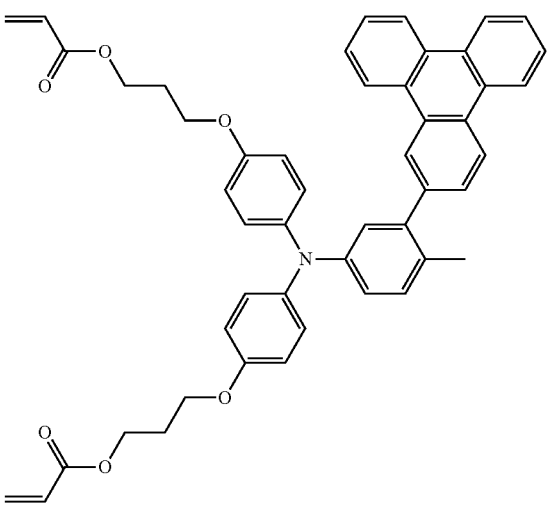
Example Compound 10
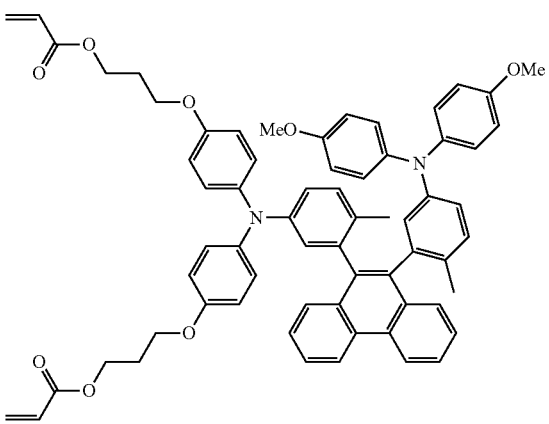

Example Compound 11
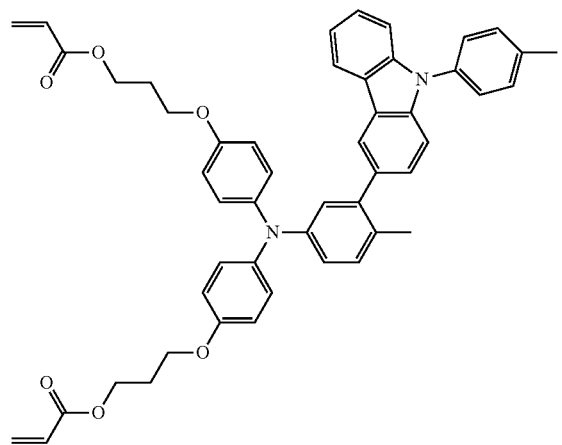
Example Compound 12
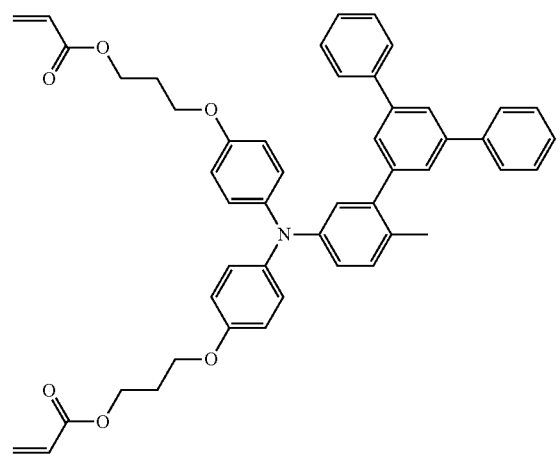
Example Compound 13
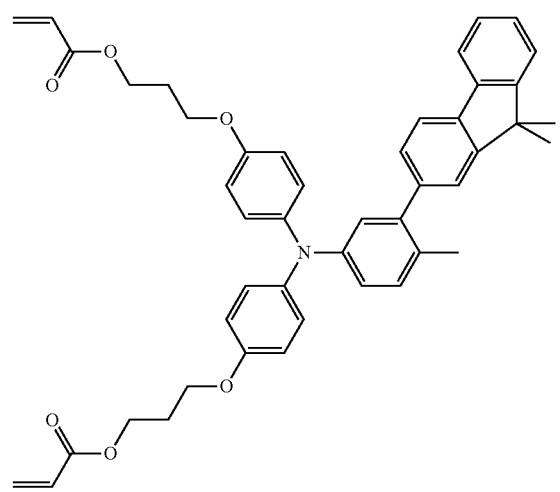
Example Compound 14
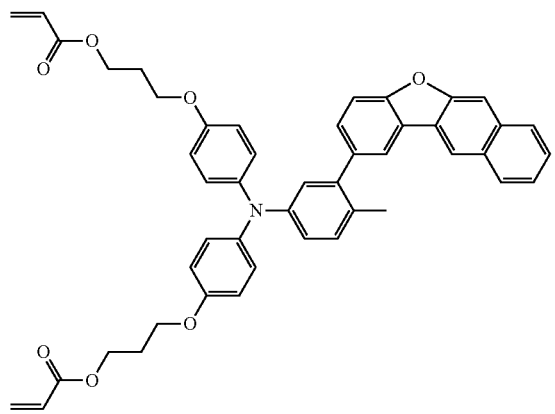
Example Compound 15
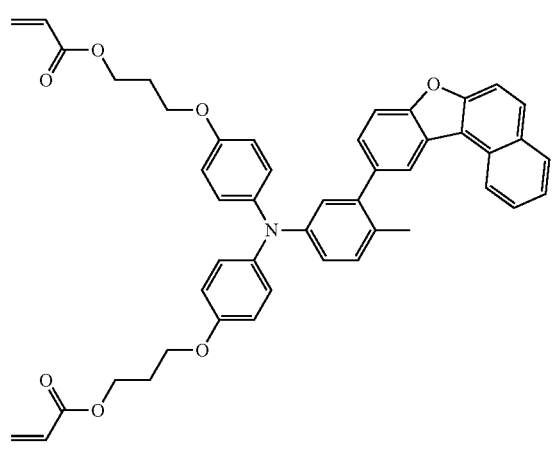
Example Compound 16
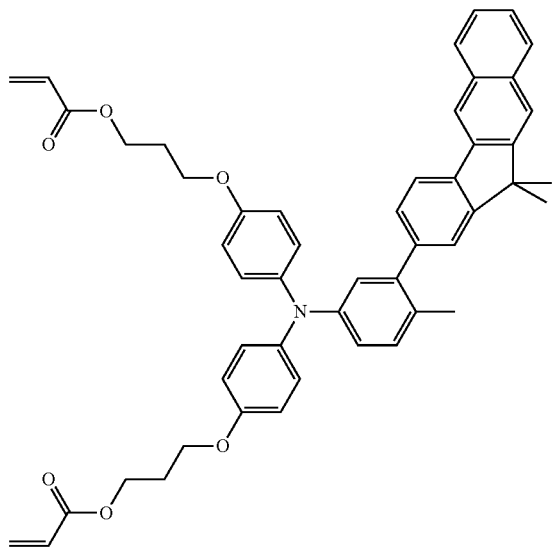

Example Compound 17
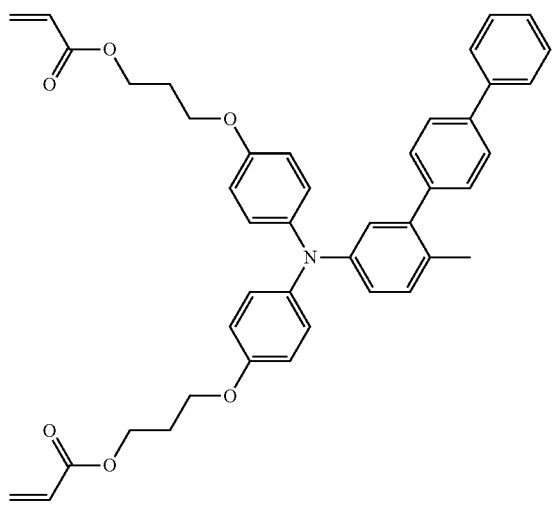
Example Compound 20
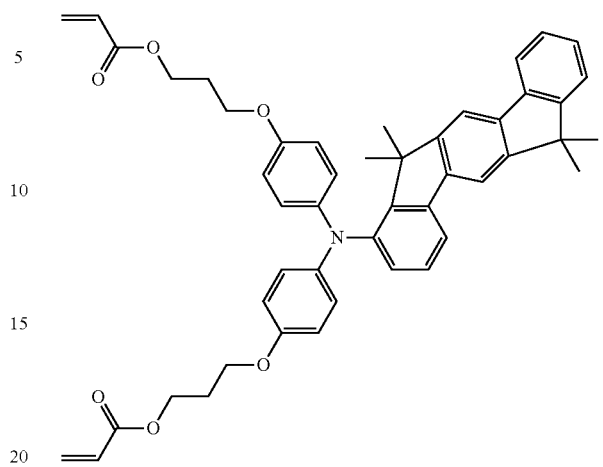
Example Compound 18
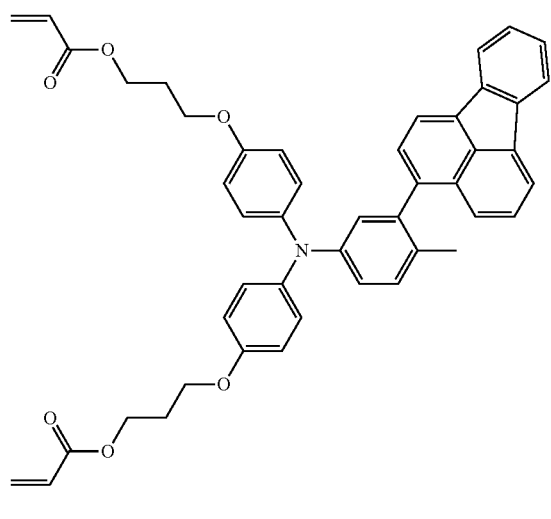
Example Compound M1
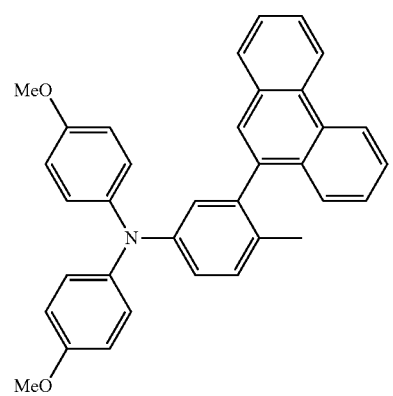
Example Compound 19
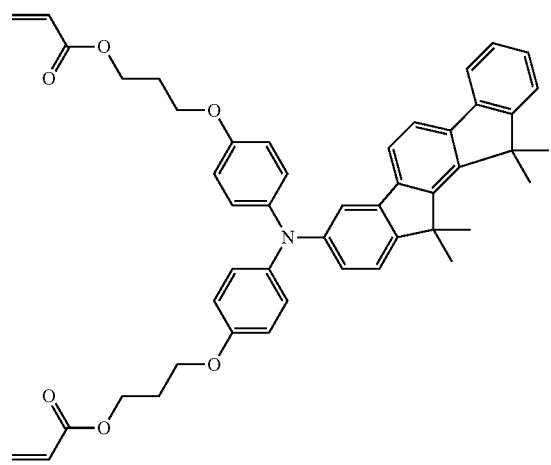
Example Compound M2
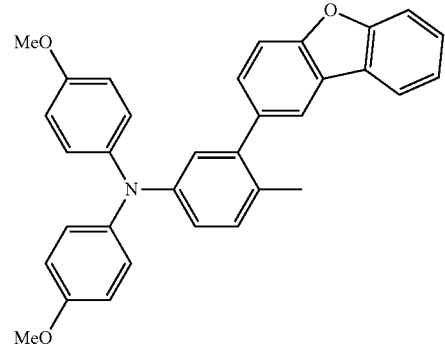

Example Compound M3

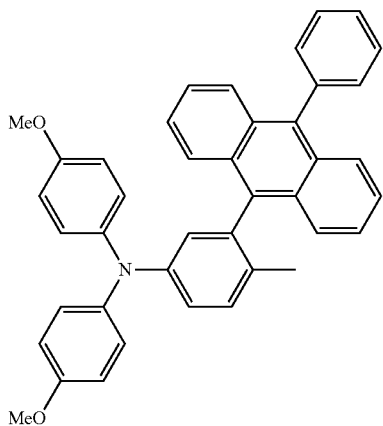

The electrochromic compound in accordance with some embodiments of the present invention has a triarylamine backbone. $R_1$ to $R_9$ and $Ar_1$ to $Ar_6$ each represent a specific element or group, and at least one of $Ar_1$ to $Ar_6$ represents a specific group. Due to this configuration, light durability and repetition durability against electrostatic charging and charge-removing that is similar to redox process are improved.

To be applied to an electrochromic element, the electrochromic compound is required to provide properties required by electrochromic elements. Electrochromic elements may require, for example, that the electrochromic composition be transparent in a neutral state and have solubility, and that electrochromic layers be stackable. The electrochromic compound in accordance with some embodiments of the present invention can provide properties required by electrochromic elements.

Electrochromic Composition

An electrochromic composition according to some embodiments of the present invention comprises the above-described electrochromic compound.

The electrochromic compound is a radical polymerizable compound having a triarylamine backbone, as described above. The electrochromic compound imparts an electrochromic function that causes a redox reaction at the surface of a first electrode of an electrochromic element, to be described later.

Preferably, the electrochromic composition further comprises another radical polymerizable compound other than the electrochromic compound (hereinafter "other radical polymerizable compound).

Other Radical Polymerizable Compound The other radical polymerizable compound is a compound having at least one radical polymerizable group, that is different from the electrochromic compound. Examples of the other radical polymerizable compound include, but are not limited to, monofunctional radical polymerizable compounds, difunctional radical polymerizable compounds, trifunctional and more-functional radical polymerizable compounds, functional monomers, and radical polymerizable oligomers. Among these compounds, difunctional and more-functional radical polymerizable compounds are preferable. Specific examples of the radical polymerizable functional group contained in the other radical polymerizable compound include those exemplified for the radical polymerizable functional group contained in the electrochromic compound. In particular, acryloyloxy group and methacryloyloxy group are preferable.

Specific examples of the monofunctional radical polymerizable compounds include, but are not limited to, 2-(2-ethoxyethoxy)ethyl acrylate, methoxypolyethylene glycol monoacrylate, methoxypolyethylene glycol monomethacrylate, phenoxypolyethylene glycol acrylate, 2-acryloyloxyethyl succinate, 2-ethylhexyl acrylate, 2-hydroxyethyl acrylate, 2-hydroxypropyl acrylate, tetrahydrofurfuryl acrylate, 2-ethylhexylcarbitol acrylate, 3-methoxybutyl acrylate, benzyl acrylate, cyclohexyl acrylate, isoamyl acrylate, isobutyl acrylate, methoxytriethylene glycol acrylate, phenoxytetraethylene glycol acrylate, cetyl acrylate, isostearyl acrylate, stearyl acrylate, and styrene monomer. Each of these compounds can be used alone or in combination with others.

Specific examples of the difunctional radical polymerizable compounds include, but are not limited to, 1,3-butanediol diacrylate, 1,4-butanediol diacrylate, 1,4-butanediol dimethacrylate, 1,6-hexanediol diacrylate, 1,6-hexanediol dimethacrylate, diethylene glycol diacrylate, polyethylene glycol diacrylate, neopentyl glycol diacrylate, EO-modified bisphenol A diacrylate, EO-modified bisphenol F diacrylate, and neopentyl glycol diacrylate. Each of these compounds can be used alone or in combination with others.

Specific examples of the trifunctional radical polymerizable compounds include, but are not limited to, trimethylolpropane triacrylate (TMPTA), trimethylolpropane trimethacrylate, EO-modified trimethylolpropane triacrylate, PO-modified trimethylolpropane triacrylate, caprolactone-modified trimethylolpropane triacrylate, HPA-modified trimethylolpropane trimethacrylate, pentaerythritol triacrylate, pentaerythritol tetraacrylate (PETTA), glycerol triacrylate, ECH-modified glycerol triacrylate, EO-modified glycerol triacrylate, PO-modified glycerol triacrylate, tris (acryloxyethyl) isocyanurate, dipentaerythritol hexaacrylate (DPHA), caprolactone-modified dipentaerythritol hexaacrylate, dipentaerythritol hydroxypentaacrylate, alkyl-modified dipentaerythritol pentaacrylate, alkyl-modified dipentaerythritol tetraacrylate, alkyl-modified dipentaerythritol triacrylate, dimethylolpropane tetraacrylate (DTMPTA), pentaerythritol ethoxytetraacrylate, EO-modified phosphoric triacrylate, and 2,2,5,5-tetrahydroxymethylcyclopentanone tetraacrylate. Each of these compounds can be used alone or in combination with others. In the above descriptions, "EO-modified" and "PO-modified" represent "ethyleneoxy-modified" and "propyleneoxy-modified", respectively.

Specific examples of the functional monomers include, but are not limited to: fluorine-substituted monomers, such as octafluoropentyl acrylate, 2-perfluorooctylethyl acrylate, 2-perfluorooctylethyl methacrylate, and 2-perfluoroisononylethyl acrylate; polysiloxane-group-containing vinyl monomers having 20 to 70 siloxane repeating units disclosed in JP-05-60503-B (corresponding to JP-62-156172-A) and JP-06-45770-B (corresponding to JP-62-290768-A), such as acryloyl polydimethylsiloxane ethyl, methacryloyl polydimethylsiloxane ethyl, acryloyl polydimethylsiloxane propyl, acryloyl polydimethylsiloxane butyl, diacryloyl polydimethylsiloxane diethyl; and acrylates and methacrylates. Each of these compounds can be used alone or in combination with others.

Specific examples of the radical polymerizable oligomers include, but are not limited to, epoxy acrylate oligomers, urethane acrylate oligomers, and polyester acrylate oligomers.

Preferably, at least one of the electrochromic compound and the other radical polymerizable compound has at least two radical polymerizable functional groups, for forming of a cross-linked product.

Preferably, the content rate of the electrochromic compound in the electrochromic composition is from 10% to 100% by mass, more preferably from 30% to 90% by mass. When the content rate is 10% by mass or more, in an electrochromic element to be described later, a first electrochromic layer exhibits sufficient electrochromic function, high durability against repeated use under application of voltage, and high color developing sensitivity. When the content rate is 100% by mass or less, the first electrochromic layer exhibits electrochromic function and excellent color developing sensitivity for its thickness. When the content rate is 100% by mass, there may be a case in which the electrochromic layer becomes less compatible with an ionic liquid that is needed for giving and receiving charge, thereby causing deterioration of durability against repeated use under application of voltage and deterioration of electric properties. Although it depends on the process with which the electrochromic element is to be used, a preferred content rate is in the range of from 30% to 90% by mass for achieving a good balance between color developing sensitivity and durability against repeated use.

Preferably, the electrochromic composition further comprises a filler and/or a polymerization initiator.

Filler

Examples of the filler include organic fillers and inorganic fillers.

Specific examples of the inorganic fillers include, but are not limited to, powders of metals (e.g., copper, tin, aluminum, and indium), metal oxides (e.g., silicon dioxide (silica), tin oxide, zinc oxide, titanium oxide, aluminum oxide (alumina), zirconium oxide, indium oxide, antimony trioxide, bismuth oxide, calcium oxide, antimony-doped tin oxide (ATO), and tin-doped indium oxide), and metal fluorides (e.g., tin fluoride, calcium fluoride, and aluminum fluoride). Each of these materials can be used alone or in combination with others. Among these materials, metal oxides are preferable, and silica, alumina, and antimony-doped tin oxide (ATO) are more preferable for transparency, stability, and ease in surface modification.

Specific examples of the organic fillers include, but are not limited to, resins (e.g., polyester, polyether, polysulfide, polyolefin, silicone, and polytetrafluoroethylene), low-molecular-weight compounds (e.g., fatty acids), and pigments (e.g., phthalocyanine). Each of these materials can be used alone or in combination with others. Among these materials, resins are preferable for transparency and insolubility. Preferably, the filler has an average primary particle diameter of 1 μm or less, more preferably from 10 nm to 1 μm. When the average primary particle diameter of the filler is 1 μm or less, the resulting layer has high surface smoothness since no coarse particle is present.

Preferably, the content of the filler in 100 parts by mass of total radical polymerizable compounds is from 0.3 to 1.5 parts by mass, more preferably from 0.6 to 0.9 parts by mass. When the content is 0.3 parts by mass or more, filler effect is sufficiently exerted and film formation property is excellent. When the content is 1.5 parts by mass of less, the rate of triarylamine compounds is appropriate and electrochemical properties of the resulting electrochromic element are excellent.

Polymerization Initiator

Preferably, the electrochromic composition comprises a polymerization initiator for improving a cross-linking reaction efficiency between the electrochromic compound and the other radical polymerizable compound. Examples of the polymerization initiator include, but are not limited to, thermal polymerization initiators and photopolymerization initiators. Photopolymerization initiators are more preferable for polymerization efficiency.

Specific examples of the thermal polymerization initiators include, but are not limited to, peroxide initiators (e.g., 2,5-dimethylhexane-2,5-dihydroperoxide, dicumyl peroxide, benzoyl peroxide, t-butylcumyl peroxide, 2,5-dimethyl-2,5-di(peroxybenzoyl)hexine-3, di-t-butyl peroxide, t-butyl hydroperoxide, cumene hydroperoxide, and lauroyl peroxide) and azo initiators (e.g., azobisisobutyronitrile, azobiscyclohexanecarbonitrile, azobis(methyl isobutyrate), azobisisobutyl amidine hydrochloride, and 4,4'-azobis-4-cyanovaleric acid). Each of these compounds can be used alone or in combination with others.

Specific examples of the photopolymerization initiators include, but are not limited to, acetophenone or ketal photopolymerization initiators (e.g., diethoxyacetophenone, 2,2-dimethoxy-1,2-diphenylethane-1-one, 1-hydroxy-cyclohexyl-phenyl-ketone, 4-(2-hydroxyethoxy)phenyl-(2-hydroxy-2-propyl) ketone, 2-benzyl-2-dimethylamino-1-(4-morpholinophenyl)butanone-1, 2-hydroxy-2-methyl-1-phenyl-propane-1-one, 2-methyl-2-morpholino(4-methylthiophenyl)propane-1-one, and 1-phenyl-1,2-propanedione-2-(o-ethoxycarbonyl)oxime), benzoin ether photopolymerization initiators (e.g., benzoin, benzoin methyl ether, benzoin ethyl ether, benzoin isobutyl ether, and benzoin isopropyl ether), benzophenone photopolymerization initiators (e.g., benzophenone, 4-hydroxybenzophenone, methyl o-benzoylbenzoate, 2-benzoyl naphthalene, 4-benzoyl biphenyl, 4-benzoyl phenyl ether, acrylated benzophenone, and 1,4-benzoyl benzene), and thioxanthone photopolymerization initiators (e.g., 2-isopropyl thioxanthone, 2-chlorothioxanthone, 2,4-dimethylthioxanthone, 2,4-diethylthioxanthone, and 2,4-dichlorothioxanthone).

Specific examples of the photopolymerization initiators further include, but are not limited to, ethylanthraquinone, 2,4,6-trimethylbenzoyldiphenylphosphine oxide, 2,4,6-trimethylbenzoylphenylethoxyphosphine oxide, bis(2,4,6-trimethylbenzoyl)phenylphosphine oxide, bis(2,4-dimethoxybenzoyl)-2,4,4-trimethylpentylphosphine oxide, methylphenylglyoxy ester, 9,10-phenanthrene, acridine compounds, triazine compounds, and imidazole compounds. Each of these compounds can be used alone or in combination with others.

In addition, a photopolymerization accelerator may be used alone or in combination with the photopolymerization initiator. Specific examples of the photopolymerization accelerator include, but are not limited to, triethanolamine, methyldimethanolamine, ethyl 4-dimethylaminobenzoate, isoamyl 4-dimethylaminobenzoate, (2-dimethylamino)ethyl benzoate, and 4,4'-dimethylaminobenzophenone.

Preferably, the content of the polymerization initiator in 100 parts by mass of total radical polymerizable compounds is from 0.5 to 40 parts by mass, more preferably from 1 to 20 parts by mass.

Other Components

The electrochromic composition may further comprise other components, such as a solvent, plasticizer, leveling agent, sensitizer, dispersant, surfactant, and/or antioxidant.

The electrochromic composition may further comprise a cross-linker to become a cross-linked product in which the electrochromic compound is cross-linked. Specific examples of the cross-linker include, but are not limited to, isocyanates, amino resins, phenol resins, amines, epoxy compounds, monofunctional acrylates and methacrylates, polyfunctional acrylates and methacrylates having at least two ethylenic unsaturated bonds per molecule, acrylic acid esters, and methacrylic acid esters. Among these compounds, isocyanates are preferable, and polyisocyanates having multiple isocyanate groups are more preferable.

The electrochromic composition can provide properties required by electrochromic elements because the electrochromic compound in accordance with some embodiments of the present invention is contained therein. Electrochromic elements may require, for example, that the electrochromic composition be transparent in a neutral state and have solubility, and that electrochromic layers be stackable, as described above.

Electrochromic Element

An electrochromic element in accordance with some embodiments of the present invention includes a first electrode, a second electrode, and an electrolyte layer disposed between the first electrode and the second electrode. The electrochromic element may further include other members. The electrochromic element may further include an electrochromic layer disposed on the first electrode. The electrochromic composition is contained in the electrolyte layer or the electrochromic layer.

The electrochromic compound in accordance with some embodiments of the present invention has excellent light durability and repetition durability, thus providing properties required by electrochromic elements. The electrochromic element uses the electrochromic compound in accordance with some embodiments of the present invention under optimum condition and position. As a result, the electrochromic element can provide better effects than conventional electrochromic elements, in particular, excellent repetition durability and light durability.

In the following description, an electrochromic element in which the electrochromic composition is contained in an electrochromic layer disposed on the first electrode is referred to as the electrochromic element according to the first embodiment. An electrochromic element in which the electrochromic composition is contained in the electrolyte layer is referred to as the electrochromic element according to the second embodiment.

Electrochromic Element According to First Embodiment

The electrochromic element according to the first embodiment is described below with reference to the drawings. In the drawings, the scale of each member may be different from the actual scale, for ease of understanding. For the sake of convenience, explanation of a layer structure will be given with the drawings in which a first substrate is illustrated on the lower side, but the arrangement of the layers is not limited thereto in the actual manufacture or use. In the following descriptions, one side of the first substrate in the thickness direction may be referred to as "upper side", and the other side may be referred to as "lower side".

FIG. 1 is a schematic cross-sectional view of the electrochromic element according to the first embodiment. Referring to FIG. 1, an electrochromic element 10A comprises a first substrate 11, a display electrode (hereinafter maybe "first electrode") 12, a first electrochromic layer 13, an electrolyte layer 14A, a second electrochromic layer 15, a counter electrode (hereinafter maybe "second electrode") 16, and a second substrate 17. These members are laminated in this order from the first substrate 11 side.

The display electrode 12 is disposed on the upper side of the first substrate 11, and the first electrochromic layer 13 is disposed on the upper side of the display electrode 12. The counter electrode 16 is disposed on the lower side of the second substrate 17, and the second electrochromic layer 15 is disposed on the lower side of the counter electrode 16. The display electrode 12 and the counter electrode 16 are facing each other with a gap therebetween. The electrolyte layer 14A is disposed between the display electrode 12 and the counter electrode 16.

In the electrochromic element 10A, the first electrochromic layer 13 is colored or bleached in response to a redox reaction occurring at the surface of the display electrode 12, and the second electrochromic layer 15 is colored or bleached in response to a redox reaction occurring at the surface of the counter electrode 16.

The members constituting the electrochromic element 10A are each described in detail below.

First Electrochromic Layer

The first electrochromic layer contains the electrochromic composition in accordance with some embodiments of the present invention. The electrochromic composition used in the first embodiment is hereinafter referred to as the "first electrochromic composition" to be distinguished from the "second electrochromic composition" used in the second embodiment.

The first electrochromic composition preferably comprises the electrochromic compound in accordance with some embodiments of the present invention and the other radical polymerizable compound, for solubility and durability of the polymerized product of the first electrochromic composition.

The first electrochromic layer on the first electrode may be either single-layered or multi-layered.

The first electrochromic layer may be disposed on either whole surface or partial surface of the first electrode.

The first electrochromic layer can be formed in the process of producing an electrochromic element to be described later. Preferably, the first electrochromic layer has an average thickness of from 0.1 to 30 μm, more preferably from 0.4 to 10 μm.

First Electrode and Second Electrode

The first electrode and the second electrode each comprise a transparent material having conductivity. Specific examples of such a material include, but are not limited to, inorganic materials such as tin-doped indium oxide (ITO), fluorine-doped tin oxide (FTO), antimony-doped tin oxide (ATO), and zinc oxide. In particular, InSnO, GaZnO, SnO, $In_2O_3$, and ZnO are preferable.

Alternatively, electrodes having improved conductivity while maintaining transparency may be used, obtained by forming a fine network structure with transparent carbon nanotube or other highly-conductive non-transmissive materials such as Au, Ag, Pt, and Cu.

The thicknesses of the first electrode and the second electrode are so adjusted that these electrodes have proper electric resistance values required for causing redox reactions in the first electrochromic layer and the second electrochromic layer. In a case in which the first electrode and the second electrode each comprise ITO, the average thicknesses thereof are preferably from 50 to 500 nm.

The first electrode and the second electrode can be formed by vacuum vapor deposition, sputtering, or ion plating. In addition, the first electrode and the second electrode can also be formed by any coating method, such as spin coating, casting, micro gravure coating, gravure coating, bar coating, roll coating, wire bar coating, dip coating, slit coating, capillary coating, spray coating, nozzle coating, or various printing methods, such as gravure printing, screen printing, flexo printing, offset printing, reverse printing, and inkjet printing.

Electrolyte Layer

The electrolyte layer comprises an electrolyte that is filling the gap between the first electrode and the second electrode. The electrolyte may fill the gap between the first electrode and the second electrode by being injected in between the first electrode and the second electrode via multiple injection holes formed on a sealing material disposed between the first electrode and the second electrode.

Specific examples of the electrolyte include, but are not limited to, inorganic ion salts (e.g., alkali metal salts and alkali-earth metal salts), quaternary ammonium salts, and supporting salts of acids and bases. More specifically, $LiClO_4$, $LiBF_4$, $LiAsF_6$, $LiPF_6$, $LiCF_3SO_3$, $LiCF_3COO$, KCl, $NaClO_3$, NaCl, $NaBF_4$, NaSCN, $KBF_4$, $Mg(ClO_4)_2$, and $Mg(BF_4)_2$, can be used.

In addition, ionic liquids can also be used as the electrolyte. In particular, organic ionic liquids are preferable because they have a molecular structure that exhibits liquidity in a wide temperature range including room temperature. Specific examples of cationic components in such organic ionic liquids include, but are not limited to, imidazole derivatives (e.g., N,N-dimethylimidazole salt, N,N-methylethylimidazole salt, and N,N-methylpropylimidazole salt), pyridinium derivatives (e.g., N,N-dimethylpyridinium salt and N,N-methylpropylpyridinium salt), and aliphatic quaternary ammonium salts (e.g., trimethylpropylammonium salt, trimethylhexylammonium salt, and triethylhexylammonium salt). Specific preferred examples of anionic components in such organic ionic liquids include, but are not limited to, fluorine-containing compounds such as $BF_4^-$, $CF_3SO_3^-$, $PF_4^-$, and $(CF_3SO_2)_2N^-$, in view of stability in the atmosphere.

Ionic liquids in which the cationic and anionic components are combined are preferably used as the electrolyte. The ionic liquid may be directly dissolved in a photopolymerizable monomer, an oligomer, or a liquid crystal material. When solubility is poor, the ionic liquid may be first dissolved in a small amount of a solvent, and thereafter mixed with a photopolymerizable monomer, an oligomer, or a liquid crystal material. Specific examples of the solvent include, but are not limited to, propylene carbonate, acetonitrile, γ-butyrolactone, ethylene carbonate, sulfolane, dioxolan, tetrahydrofuran, 2-methyltetrahydrofuran, dimethylsulfoxide, 1,2-dimethoxyethane, 1,2-ethoxymethoxyethane, polyethylene glycol, alcohols, and mixed solvents thereof.

The electrolyte need not necessarily be a low-viscosity liquid and may be in the form of a gel, cross-linked polymer, or liquid crystal dispersion. The electrolyte in the form of a gel or solid is advantageous for improving strength and reliability of the element. Preferably, the electrolyte and the solvent are held in a polymer resin for reliable fixation. Such an electrolyte layer provides high ion conductivity and solid strength. It is preferable that the polymer resin is a photocurable resin. This is because a photocurable resin can be formed into a thin layer at a lower temperature within a shorter time period compared to a case in which a thin layer is formed by thermal polymerization and/or solvent evaporation. Preferably, the electrolyte layer has an average thickness of from 100 nm to 10 μm.

Second Electrochromic Layer

The second electrochromic layer on the second electrode may be either single-layered or multi-layered. The second electrochromic layer may be disposed on either whole surface or partial surface of the second electrode.

The second electrochromic layer contains a second electrochromic compound that is a viologen compound represented by the following formula (I). More specifically, the second electrochromic layer comprises an electrochromic composite body comprising a conductive or semiconductive nanostructural body containing the viologen compound. The viologen compound represented by the formula (I) is bindable or adsorbable to the conductive or semiconductive nanostructural body. The electrochromic composite body develops blue color in the electrochromic element, thus providing excellent image memory property, i.e., color image maintainability.

Viologen Compound

The viologen compound is described in detail below.

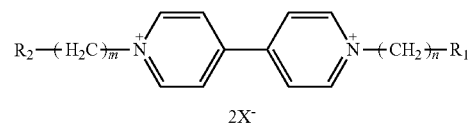

Formula (I)

In the formula (I), each of $R_1$ and $R_2$ independently represents a functional group bindable to a hydrogen atom, an aryl group having 14 carbon atoms at most, a heteroaryl group, a branched alkyl group having 10 carbon atoms at most, an alkenyl group, a cycloalkyl group, or hydroxyl group; each of n and m independently represents an integer of from 0 to 10; and $X^-$ represents an ion that neutralizes charge.

Preferably, at least one of $R_1$ and $R_2$ represents a functional group bindable to hydroxyl group. In this case, the viologen compound is adsorbable or fixable to a transparent electrode (e.g., ITO). Such a viologen compound is advantageously adsorbable or fixable to the transparent electrode even when carrier particles comprising metal oxides are disposed on the transparent electrode. More preferably, both of $R_1$ and $R_2$ each represent a functional group bindable to hydroxyl group.

Specific examples of the functional group bindable to hydroxyl group include, but are not limited to, phosphonate group, phosphate group, carboxyl group, sulfonyl group, silyl group, silanol group. Among these groups, phosphonate group, phosphate group, and carboxyl group are preferable, and phosphonate group is most preferable, in view of ease of synthesis, adsorptivity to carrier particles comprising metal oxides disposed on the transparent electrode, and stability of the compound.

Specific examples of the phosphonate group include, but are not limited to, methylphosphonate group, ethylphosphonate group, propylphosphonate group, hexylphosphonate group, octylphosphonate group, decylphosphonate group, dodecylphosphonate group, octadecylphosphonate group, benzylphosphonate group, phenylethylphosphonate group, phenylpropylphosphonate group, and biphenylphosphonate group.

Specific examples of the phosphate group include, but are not limited to, methylphosphate group, ethylphosphate group, propylphosphate group, hexylphosphate group, octylphosphate group, decylphosphate group, dodecylphosphate group, octadecylphosphate group, benzylphosphate group, phenylethylphosphate group, phenylpropylphosphate group, and biphenylphosphate group.

Specific examples of the carboxyl group include, but are not limited to, methylcarboxyl group, ethylcarboxyl group, propylcarboxyl group, hexylcarboxyl group, octylcarboxyl group, decylcarboxyl group, dodecylcarboxyl group, octadecylcarboxyl group, benzylcarboxyl group, phenylethylcarboxyl group, phenylpropylcarboxyl group, biphenylcarboxyl group, 4-propylphenylcarboxyl group, and 4-propylbiphenylcarboxyl group.

Specific examples of the sulfonyl group include, but are not limited to, methylsulfonyl group, ethylsulfonyl group, propylsulfonyl group, hexylsulfonyl group, octylsulfonyl group, decylsulfonyl group, dodecylsulfonyl group, octadecylsulfonyl group, benzylsulfonyl group, phenylethylsulfonyl group, phenylpropylsulfonyl group, and biphenylsulfonyl group.

Specific examples of the silyl group include, but are not limited to, methylsilyl group, ethylsilyl group, propylsilyl group, hexylsilyl group, octylsilyl group, decylsilyl group, dodecylsilyl group, octadecylsilyl group, benzylsilyl group, phenylethylsilyl group, phenylpropylsilyl group, and biphenylsilyl group.

Specific examples of the silanol group include, but are not limited to, methyl silanol group, ethylsilanol group, propylsilanol group, hexylsilanol group, octylsilanol group, decylsilanol group, dodecylsilanol group, octadecylsilanol group, benzylsilanol group, phenylethylsilanol group, phenylpropylsilanol group, and biphenylsilanol group.

In the formula (I), the ion $X^-$ for neutralizing charge represents a monovalent anion capable of forming a stable pair with a cationic portion. Specific examples of the ion $X^-$ for neutralizing charge include, but are not limited to, Br ion ($Br^-$), Cl ion ($Cl^-$), I ion ($I^-$), OTf (triflate) ion ($OTf^-$), $ClO_4$ ion ($ClO_4^-$), $PF_6$ ion ($PF_6^-$), and $BF_4$ ion ($BF_4^-$).

Preferably, the viologen compound is a symmetric system having an alkyl chain with a specific length. In this case, preferably, each of m and n in the formula (I) independently represents an integer of from 4 to 10, more preferably m and n represent the same integer.

Specific examples of the viologen compound include, but are not limited to, the following Example Compounds A to K.

Example Compound A

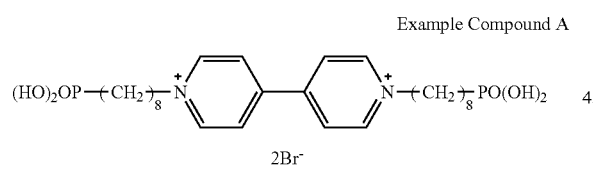

Example Compound B

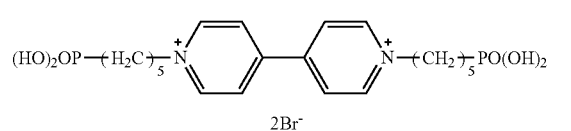

Example Compound C

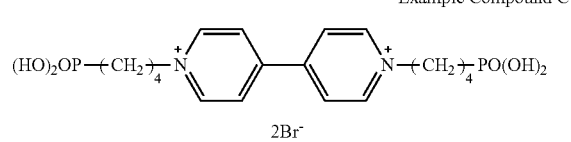

Example Compound D

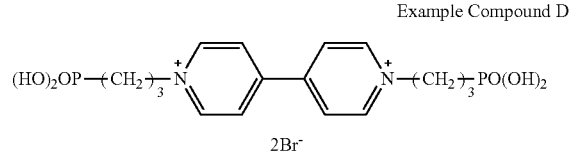

Example Compound E

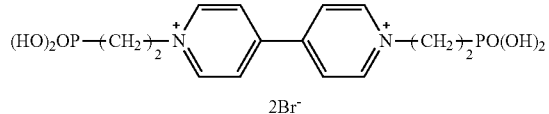

Example Compound F

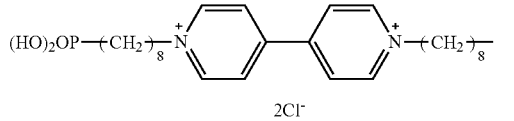

Example Compound G

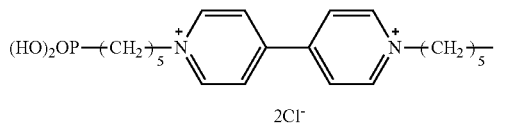

Example Compound H

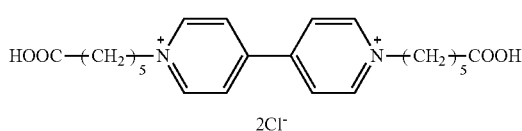

Example Compound I

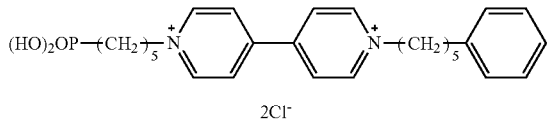

Example Compound J

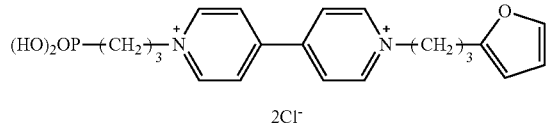

Example Compound K

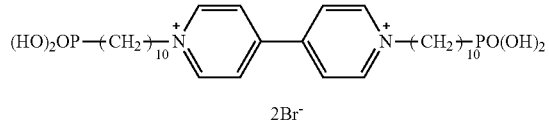

Conductive or Semiconductive Nanostructural Body

The conductive or semiconductive nanostructural body is described in detail below.

Preferably, the conductive or semiconductive nanostructural body is transparent.

In accordance with some embodiments, in the formula (I), at least one of $R_1$ and $R_2$ may represent a functional group bindable to hydroxyl group. Such a viologen compound may bind or adsorb to the conductive or semiconductive nanostructural body via phosphonate group, sulfonate group, phosphate group, carboxyl group, etc. In this case, the second electrochromic compound can be easily combined with the nanostructural body, thus providing an electrochromic composite body having excellent color image maintainability.

A plurality of phosphonate groups, sulfonate groups, phosphate groups, carboxyl groups, etc., may be contained in the viologen compound. In a case in which the viologen compound has silyl group or silanol group, the viologen compound can be strongly bound to the nanostructural body via siloxane bond, thus providing an electrochromic composite body having good stability. Here, siloxane bond refers to a chemical bond between a silicon atom and an oxygen atom.

The electrochromic composite body is not limited in bonding structure or configuration so long as it has a configuration in which the viologen compound and the nanostructural body are bound to each other via siloxane bond.

The conductive or semiconductive nanostructural body refers to a structural body having nanometer-scale irregularities. Examples thereof include nano particles and nanoporous bodies. The conductive or semiconductive nanostructural body preferably comprises a metal oxide, for transparency and conductivity.

Specific examples of the metal oxide include, but are not limited to, titanium oxide, zinc oxide, tin oxide, zirconium oxide, cerium oxide, yttrium oxide, boron oxide, magnesium oxide, strontium titanate, potassium titanate, barium titanate, calcium titanate, calcium oxide, ferrite, hafnium oxide, tungsten oxide, iron oxide, copper oxide, nickel oxide, cobalt oxide, barium oxide, strontium oxide, vanadium oxide, indium oxide, aluminosilicate, and calcium phosphate. Each of these materials can be used alone or in combination with others. For electric properties (e.g., electric conductivity) and physical properties (e.g., optical property), titanium oxide, zinc oxide, tin oxide, zirconium oxide, iron oxide, magnesium oxide, indium oxide, and tungsten oxide are preferable, and titanium oxide is most preferable. When such a metal oxide or a mixture of these metal oxides is used, a much higher response speed is provided in coloring and bleaching.

Preferably, the metal oxide is in the form of fine particles having an average primary particle diameter of 30 nm or less. As the average primary particle diameter of the metal oxide becomes smaller, light transmittance of the metal oxide is improved and the surface area per unit volume (hereinafter "specific surface area") of the electrochromic composite body is increased. As the specific surface area becomes larger, the second electrochromic compound can be carried by the nanostructural body in a more efficient manner, thus providing a multi-color display with an excellent display contrast ratio between coloring and bleaching. Preferably, the specific surface area of the nanostructural body is 100 $m^2/g$ or more.

The average primary particle diameter of the metal oxide is determined by observing 100 randomly-selected fine particles of the metal oxide with a transmission electron microscope (TEM) to measure projected areas of the fine particles, calculating a circle-equivalent diameter of each area, and averaging the calculated circle-equivalent diameter values.

The second electrochromic layer can be formed by vacuum vapor deposition, sputtering, or ion plating. The second electrochromic layer can be formed by any coating method such as spin coating, casting, micro gravure coating, gravure coating, bar coating, roll coating, wire bar coating, dip coating, slit coating, capillary coating, spray coating, nozzle coating, and various printing methods such as gravure printing, screen printing, flexo printing, offset printing, reverse printing, and inkjet printing.

Preferably, the second electrochromic layer has an average thickness of from 0.2 to 5.0 µm. When the average thickness is 0.2 µm or greater, proper coloring density can be achieved. When the average thickness is 5.0 µm or less, either an increase of manufacturing cost or a decrease of visibility caused due to coloring can be suppressed. The second electrochromic layer can be formed by means of vacuum film formation or coating of a particle-dispersed paste. The coating is more preferable in terms of productivity.

First Substrate and Second Substrate

The first substrate and the second substrate each have a function of supporting the first electrode, the first electrochromic layer, the second electrode, the second electrochromic layer, etc. The substrate comprises a transparent material capable of supporting these layers. Examples of such a material include known organic and inorganic materials.

Specific examples of the substrate include, but are not limited to, glass substrates made of non-alkali-glass, borosilicate glass, float glass, or soda-lime glass. Specific examples of the substrate further include, but are not limited to, resin substrates made of polycarbonate resin, acrylic resin, polyethylene resin, polyvinyl chloride resin, polyester resin, epoxy resin, melamine resin, phenol resin, polyurethane resin, or polyimide resin. The substrate may have a surface coating such as a transparent insulating layer, a UV cut layer, and/or an antireflection layer, for improving vapor barrier property, gas barrier property, ultraviolet resistance, and visibility.

The substrate is not limited in planer shape, and may have a rectangular shape or a circular shape. The substrate may be a laminated body of multiple materials. As an example, an electrochromic element that is sandwiched by two glass substrates provides improved vapor barrier property and gas barrier property.

Other Members

The electrochromic element may further include other members, such as an insulating porous layer, an anti-deterioration layer, and a protective layer.

Insulating Porous Layer

The insulating porous layer has a function of electrically insulating the first electrode and the second electrode from each other and another function of holding the electrolyte. The insulating porous layer comprises a porous material. In particular, organic, inorganic, or organic-inorganic composite materials having high insulation property, durability, and film-formation property are preferably used.

The insulating porous layer can be formed by: a sintering method in which polymer fine particles or inorganic particles are partially fused with each other via a binder to form pores between the particles; or an extraction method in which solvent-soluble organic or inorganic substances and solvent-insoluble binders are formed into a layered structure, and the organic or inorganic substances are dissolved with a solvent to form pores. The insulating porous layer can also be formed by: a foaming method; a phase inversion method in which a mixture of polymers is subjected to phase separation by handling a good solvent and a poor solvent; or a radiation irradiation method in which pores are formed by means of radiation.

Anti-Deterioration Layer

The function of the anti-deterioration layer is to undergo the reverse reaction of a reaction occurring in the first electrochromic layer or the second electrochromic layer to balance the charges therebetween, so that the first electrode or the second electrode are prevented from being corroded or degraded by an irreversible redox reaction. The reverse reaction includes both a redox reaction of the anti-deterioration layer and an action thereof as a capacitor.

The anti-deterioration layer comprises a material having a function of preventing the first electrode and the second electrode from being corroded by an irreversible redox reaction occurring therein. Specific examples of such a material include, but are not limited to, antimony tin oxide, nickel oxide, titanium oxide, zinc oxide, tin oxide, and conductive or semiconductive metal oxides containing two or more of these materials. The anti-deterioration layer may comprise a porous thin film which does not inhibit injection of an electrolyte. Such a porous thin film having excellent electrolyte permeability and anti-deterioration property can be obtained by, for example, fixing fine particles of a conductive or semiconductive metal oxide (e.g., antimony-tin oxide, nickel oxide, titanium oxide, zinc oxide, and tin oxide) on the second electrode with a binder (e.g., acrylic binder, alkyd binder, isocyanate binder, urethane binder, epoxy binder, and phenol binder).

Protective Layer

The protective layer has functions of protecting the electrochromic element from external stress and chemicals used in the washing process, preventing the electrolyte from leaking from the electrochromic element, and preventing the electrochromic element from being intruded by unnecessary substances, such as moisture and oxygen in the air, for its stable operation.

The protective layer may comprise an ultraviolet-curable or heat-curable resin such as acrylic resin, urethane resin, and epoxy resin.

Preferably, the protective layer has an average thickness of from 1 to 200 µm.

Method for Manufacturing Electrochromic Element According to First Embodiment

A method for manufacturing the electrochromic element according to the first embodiment is described below.

First, the first electrode 12 is formed on the first substrate 11. Next, the first electrode 12 is coated with a coating liquid containing the first electrochromic composition containing the electrochromic compound in accordance with some embodiments of the present invention and other radical polymerizable compound. Thus, a first laminated body is prepared in which the first electrode 12 and the first electrochromic layer 13, in this order, are formed on the first substrate 11.

Specific examples of the electrochromic compound and other radical polymerizable compound used here include the above-exemplified materials for the electrochromic element according to the first embodiment.

The coating liquid may be diluted with a solvent, if necessary, before being applied. Specific examples of the solvent include, but are not limited to, alcohol solvents (e.g., methanol, ethanol, propanol, and butanol), ketone solvents (e.g., acetone, methyl ethyl ketone, methyl isobutyl ketone, and cyclohexanone), ester solvents (e.g., ethyl acetate and butyl acetate), ether solvents (e.g., tetrahydrofuran, dioxane, and propyl ether), halogen solvents (e.g., dichloromethane, dichloroethane, trichloroethane, and chlorobenzene), aromatic solvents (e.g., benzene, toluene, and xylene), and cellosolve solvents (e.g., methyl cellosolve, ethyl cellosolve, and cellosolve acetate). Each of these solvents can be used alone or in combination with others.

The rate of dilution is determined depending on solubility of the first electrochromic composition, coating method, and a target thickness of the first electrochromic layer.

The coating method may be, for example, dip coating, spray coating, bead coating, and ring coating.

The method for manufacturing the electrochromic element according to the first embodiment may further include a cross-linking process for cross-linking the first electrochromic composition by externally applying energy thereto.

In the cross-linking process, the first electrochromic composition applied to the first electrode is cured by externally applying energy thereto, thus forming a first electrochromic layer. Examples of the external energy include, but are not limited to, thermal energy, optical energy, and radial rays. Thermal energy can be applied by heating the coating liquid having applied to the first electrode from the coated-surface side or the opposite substrate-side of the first electrode, using a gaseous substance (e.g., air and nitrogen gas), vapor, a heat medium, infrared ray, or electromagnetic wave.

In this case, preferably, the heating temperature is in the range of from 60° C. to 170° C. Optical energy can be applied from a UV light source having light-emitting wavelengths in the ultraviolet rage, such as a high-pressure mercury lamp and a metal halide lamp, or a visible light source emitting light corresponding to the absorption wavelength of the radical polymerizable compounds or a photopolymerization initiator. In this case, preferably, the amount of UV light emission is in the range of from 5 to 15,000 mW/cm$^2$.

Next, the second electrode 16 is formed on the second substrate 17. The second electrode 16 is thereafter coated with a coating liquid containing the electrochromic composite body comprising the second electrochromic composition and the conductive or semiconductive nanostructural body. Thus, a second laminated body is prepared in which the second electrode 16 and the second electrochromic layer 15, in this order, are formed on the second substrate 17.

Specific examples of the second electrochromic compound and conductive or semiconductive nanostructural body used here include the above-exemplified materials for the electrochromic element according to the first embodiment.

Next, the gap between the first laminated body and the second laminated body is filled with an electrolyte liquid, so that the first laminated body and the second laminated body are disposed via the electrolyte layer 14A. Thus, the electrochromic element 10A is prepared. In a case in which the electrolyte constituting the electrolyte layer 14A is curable by light or heat, the electrolyte is cured after the first laminated body and the second laminated body are bonded to each other via the electrolyte.

The method for manufacturing the electrochromic element according to the present embodiment may further include other processes.

For example, in a case in which the electrochromic element 10A further comprises an insulating porous layer, the method may further include a process of forming the insulating porous layer on the first electrochromic layer 13. Alternatively, the method may include a process of forming the insulating porous layer on the lower side of the second electrochromic layer 15, or by mixing with the electrolyte constituting the electrolyte layer 14A.

In a case in which the electrochromic element 10A further comprises an anti-deterioration layer and/or a protective layer, the method may include a process of forming these layers in the electrochromic element 10A.

Electrochromic Element According to Second Embodiment

The electrochromic element according to the second embodiment is described below with reference to the drawings. An electrochromic element 10B according to the second embodiment, illustrated in FIG. 2, is different from the electrochromic element 10A according to the first embodiment, illustrated in FIG. 1, in that the first electrochromic layer 13 is omitted and the electrolyte layer 14A is replaced with another electrolyte layer 14B containing the electrochromic composition in accordance with some embodiments of the present invention.

Figure 2:
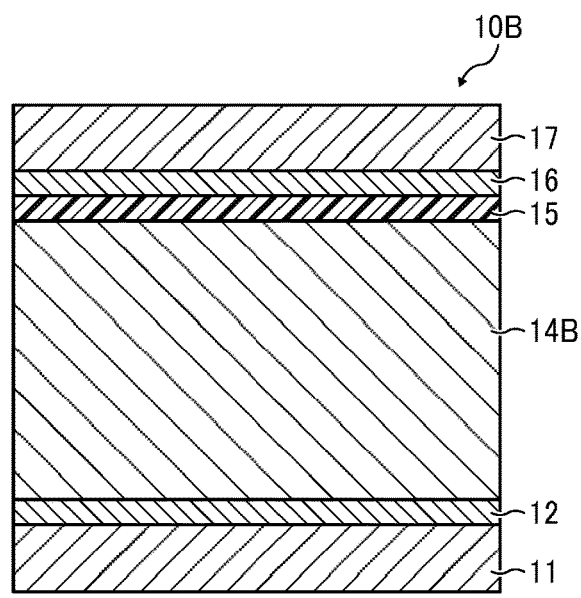
FIG. 2 is a schematic cross-sectional view of an electrochromic element in accordance with a second embodiment of the present invention.

FIG. 2 is a schematic cross-sectional view of the electrochromic element according to the second embodiment. Referring to FIG. 2, the electrochromic element 10B comprises a first substrate 11, a display electrode 12, an electrolyte layer 14B, a second electrochromic layer 15, a counter electrode 16, and a second substrate 17. These members are laminated in this order from the first substrate 11 side. The electrolyte layer 14B contains the electrochromic composition in accordance with some embodiments of the present invention and an electrolyte. Since the other members constituting the electrochromic element 10B are the same as those constituting the electrochromic element 10A, detailed explanations thereof are omitted.

Method for Manufacturing Electrochromic Element According to Second Embodiment

A method for manufacturing the electrochromic element according to the second embodiment is described below. The method includes no process of forming the first electrochromic layer 13 that is formed in the electrochromic element 10A according to the first embodiment. The method includes a process of forming the electrolyte layer 14B containing the electrochromic composition in accordance with some embodiments of the present invention, in place of the electrolyte layer 14A.

First, the first electrode 12 is formed on the first substrate 11. Next, the second electrode 16 and the second electrochromic layer 15, in this order, are formed on the second substrate 17 to prepare a second laminated body.

Next, an electrolyte liquid comprising the electrochromic composition in accordance with some embodiments of the present invention and an electrolyte are prepared. The gap between the first electrode 12 and the second laminated body is filled with the electrolyte liquid, so that the first electrode 12 and the second laminated body are disposed via the electrolyte layer 14B. Thus, the electrochromic element 10B is prepared.

The electrochromic elements in accordance with some embodiments of the present invention have excellent light durability and repetition durability. The electrochromic elements can be used for, for example, electrochromic display, large-size displays such as stock price display, anti-glare mirror, and light control elements such as light control glass.

In addition, the electrochromic elements can be preferably used for low-voltage driving elements such as touch-panel-type key switch, optical switch, optical memory, electronic paper, and electronic album.

EXAMPLES

Further understanding of the present disclosure can be obtained by reference to certain specific examples provided herein below for the purpose of illustration only and are not intended to be limiting.

Example 1

Synthesis Example 1

Synthesis of Electrochromic Compound 1

An electrochromic compound 1 was synthesized according to the following synthesis scheme (1).

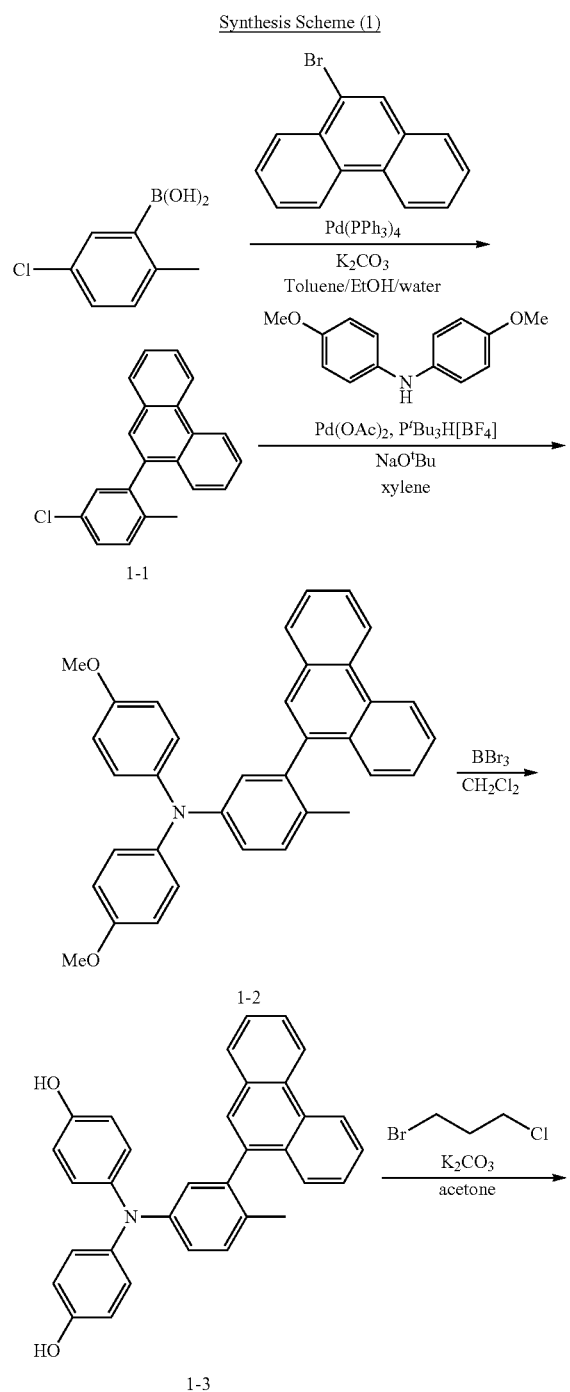

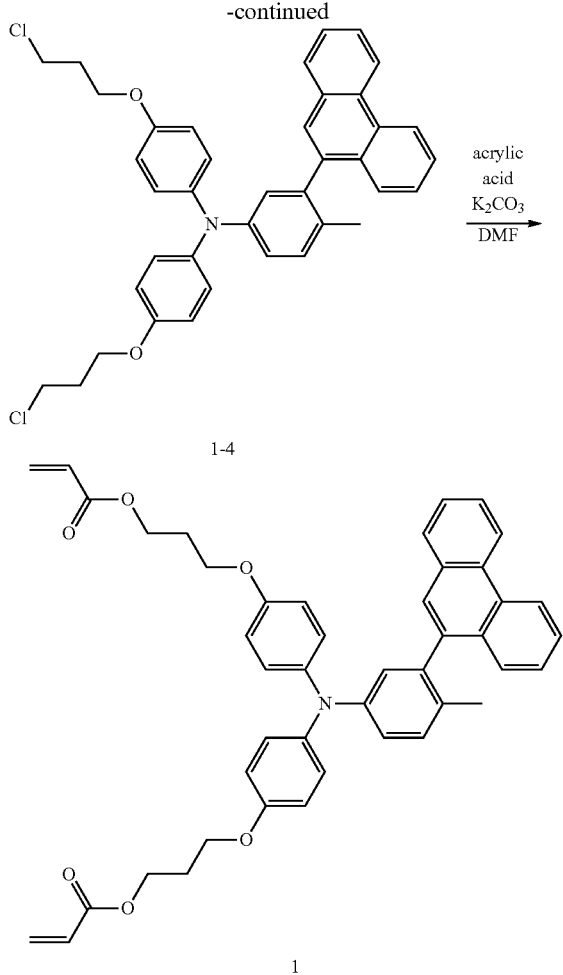

Synthesis of Compound 1-1

A four-neck flask was charged with 4-chloro-2-methylphenylboronic acid (product of Tokyo Chemical Industry Co., Ltd., 1.70 g, 10 mmol), 9-bromophenanthrene (2.57 g, 10 mmol), and potassium carbonate (product of Kanto Chemical Co., Inc., 4.15 g, 30 mmol). The air in the flask was then replaced with argon gas. Toluene (35 mL), ethanol (10 mL), and water (5 mL) were further added to the flask and bubbling was performed with argon gas for 10 minutes. Tetrakis(triphenylphosphine)palladium(0) (product of Tokyo Chemical Industry Co., Ltd., 116 mg, 0.1 mmol) was further added to the flask, and the flask was heated to an inner temperature of about 90° C. for 2.5 hours under reflux. After adding 4-chloro-2-methylphenylboronic acid (170 mg, 1 mmol) to the flask, the heating was continued for 2 hours at the same temperature. The liquid in the flask was cooled to room temperature and mixed with ethyl acetate and water. After separating the organic phase, the aqueous phase was extracted with ethyl acetate 3 times. The collected organic phases were washed with water once and thereafter with a saturated salt solution once. The organic phase was dried with anhydrous sodium sulfate and, after the drying agent was separated, condensed under reduced pressures. The residue was dissolved in a mixed solvent of hexane and ethyl acetate (hexane/ethyl acetate=98/2 by volume) and purified by a silica gel chromatography. Thus, a compound 1-1, that was a colorless amorphous body, was prepared (yield: 2.99 g, 98.6%).

Synthesis of Compound 1-2

A four-neck flask was charged with the above-prepared compound 1-1 (2.90 g, 9.8 mmol), 4,4'-dimethoxydiphenylamine (product of Tokyo Chemical Industry Co., Ltd., 2.26 g, 9.8 mmol), palladium acetate (product of Tokyo Chemical Industry Co., Ltd., 23 mg, 0.1 mmol), and tri-tert-butylphosphonium tetrafluoroborate (product of Tokyo Chemical Industry Co., Ltd., 87 mg, 0.30 mmol). The air in the flask was then replaced with argon gas. Xylene (20 mL) was further added to the flask and bubbling was performed with argon gas for 10 minutes. After heating the liquid in the flask to 70° C., sodium tert-butoxide (product of Tokyo Chemical Industry Co., Ltd., 1.88 g, 19.6 mmol) was added to the flask. The liquid was heated for 5.5 hours in a bath having a temperature of 120° C. The liquid was thereafter cooled to room temperature and filtered with silica gel. The silica gel was washed with toluene, and the collected filtrate was condensed under reduced pressures. The residue was dissolved in a mixed solvent of hexane and toluene (hexane/toluene=4/6 by volume) and purified by a silica gel chromatography. In the silica gel chromatography, a gradient method was employed in which the composition of the mobile phase was changed. Specifically, the ratio (hexane:toluene) between hexane and toluene was changed from 4:6 to 6:4. The purified residue was thereafter dried under reduced pressures. Thus, a compound 1-2, that was a colorless amorphous body, was prepared (yield: 2.88 g, 59.4%).

The compound 1-2 was identified by a nuclear magnetic resonance spectrometer $^1$H-NMR (product of JEOL Ltd., 500 MHz) and a mass spectrometer (LCT-Premier with ASAP Probe, product of Waters Corporation). As a result, it was confirmed from the identified structure and molecular weight that the obtained compound was the objective compound 1-2.

Synthesis of Compound 1-3

A four-neck flask was charged with the compound 1-2 (2.476 g, 5 mmol) and dichloromethane (40 mL) under argon atmosphere. The liquid was cooled to −5° C. Next, 1M BBr$_3$ (40 mL of dichloromethane solution) was dropped therein over a period of 20 minutes. The liquid was stirred for 1 hour at the same temperature, and further stirred 1 hour after being heated to room temperature. The liquid was cooled to 0° C. again, and methanol (40 mL) was dropped therein. After removing the solvent under reduced pressures, ethyl acetate and a saturated aqueous solution of sodium hydrogen carbonate were added thereto.

The organic phase was separated and the aqueous phase was extracted with ethyl acetate twice. The collected organic phases were washed with the saturated aqueous solution of sodium hydrogen carbonate twice and thereafter with a saturated salt solution. The organic phase was dried with sodium sulfate and, after the drying agent was separated, condensed. Thus, a compound 1-3 was prepared (yield: 2.85 g, 122%).

The compound 1-3 was identified by a nuclear magnetic resonance spectrometer $^1$H-NMR (product of JEOL Ltd., 500 MHz) and a mass spectrometer (LCT-Premier with ASAP Probe, product of Waters Corporation). As a result, it was confirmed from the identified structure and molecular weight that the obtained compound was the objective compound 1-3.

Synthesis of Compound 1-4

A four-neck flask was charged with the compound 1-3 (2.85 g, 5 mmol), acetone (40 mL), 1-bromo-chloropropane (6.28 g, 40 mmol), and potassium carbonate (6.35 g, 46.4 mmol) under argon atmosphere. The liquid was stirred for 9 hours in a bath having a temperature of 60° C. The liquid was then cooled to room temperature and filtered. The filtrate was condensed. The obtained oil was dissolved in hexane and purified by a column chromatography. In the column chromatography, a gradient method was employed in which the composition of the mobile phase was changed. Specifically, the composition of the solvent was changed from hexane alone to a mixture of hexane and toluene (hexane:toluene=3:7). The purified residue was thereafter dried under reduced pressures. Thus, a compound 1-4, that was a colorless amorphous body, was prepared (yield: 2.95 g, 95.0%).

The compound 1-4 was identified by a nuclear magnetic resonance spectrometer $^1$H-NMR (product of JEOL Ltd., 500 MHz) and a mass spectrometer (LCT-Premier with ASAP Probe, product of Waters Corporation). As a result, it was confirmed from the identified structure and molecular weight that the obtained compound was the objective compound 1-4.

Synthesis of Compound 1

A four-neck flask was charged with the compound 1-4 (2.95 g, 4.75 mmol), acrylic acid (2.05 g), dibutylhydroxytoluene (hereinafter "BHT", 3 mg), dimethylformamide (hereinafter "DMF", 300 mL), and potassium carbonate (4.73 g). The liquid was stirred for 10 hours in a bath having a temperature of 85° C. The liquid in the flask was cooled to room temperature and mixed with ethyl acetate, hexane, and water. After separating the organic phase, the aqueous phase was extracted with ethyl acetate 3 times. The collected organic phases were washed with water twice and thereafter with a saturated salt solution once. The organic phase was dried and, after the drying agent was separated, condensed. The obtained residue was dissolved in hexane and purified by a column chromatography. In the column chromatography, a gradient method was employed in which the composition of the mobile phase was changed. Specifically, the composition of the solvent was changed from hexane alone to a mixture of hexane and ethyl acetate (hexane:ethyl acetate=65:35). After adding BHT (2.2 mg), the eluate was condensed and dried at 40° C. under reduced pressures and light shielding. Thus, a compound 1, that was a colorless viscous oil, was prepared (yield: 2.93 g, 89.0%).

The compound 1 was identified by a nuclear magnetic resonance spectrometer $^1$H-NMR (product of JEOL Ltd., 500 MHz) and a mass spectrometer (LCT-Premier with ASAP Probe, product of Waters Corporation). As a result, it was confirmed from the identified structure and molecular weight that the obtained compound was the objective compound 1.

Synthesis Example 2

Synthesis of Electrochromic Compound 2

An electrochromic compound 2 was synthesized according to the following synthesis scheme (2).

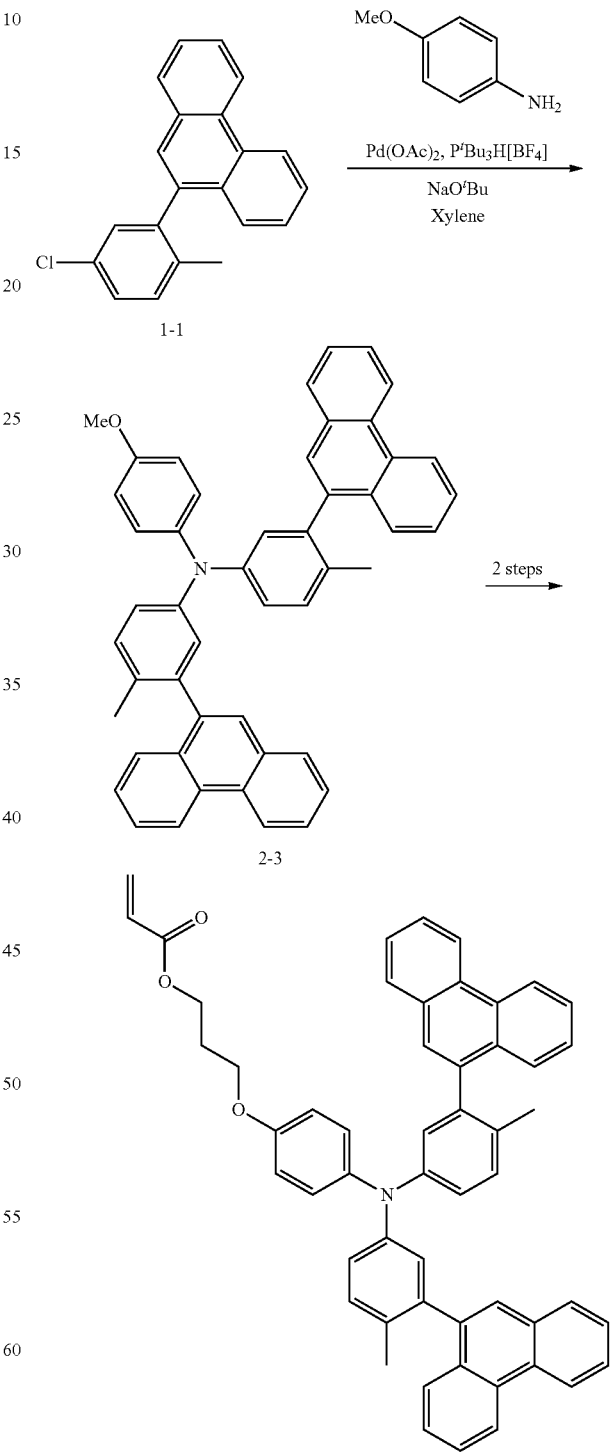

Synthesis of Compound 2-3

The procedure for preparing the compound 1-2 was repeated except for changing the equivalent amount of the compound 1-1 to two equivalents and replacing 4,4'-dimethoxydiphenylamine with 4-methoxyaniline. Thus, a compound 2-3, that was a colorless amorphous body, was prepared (yield: 3.3 g, 60%).

The compound 2-3 was identified by a nuclear magnetic resonance spectrometer $^1$H-NMR (product of JEOL Ltd., 500 MHz) and a mass spectrometer (LCT-Premier with ASAP Probe, product of Waters Corporation). As a result, it was confirmed from the identified structure and molecular weight that the obtained compound was the objective compound 2-3.

Synthesis of Compound 2

The procedure for preparing the compound 1 was repeated except for replacing the compound 1-3 with the compound 2-3. Thus, a compound 2, that was a colorless viscous oil, was prepared (yield: 4.2 g, 90.0%).

The compound 2 was identified by a nuclear magnetic resonance spectrometer $^1$H-NMR (product of JEOL Ltd., 500 MHz) and a mass spectrometer (LCT-Premier with ASAP Probe, product of Waters Corporation). As a result, it was confirmed from the identified structure and molecular weight that the obtained compound was the objective compound 2.

Synthesis Example 3

Synthesis of Electrochromic Compound 3

An electrochromic compound 3 was synthesized according to the following synthesis scheme (3).

Synthesis Scheme (3)

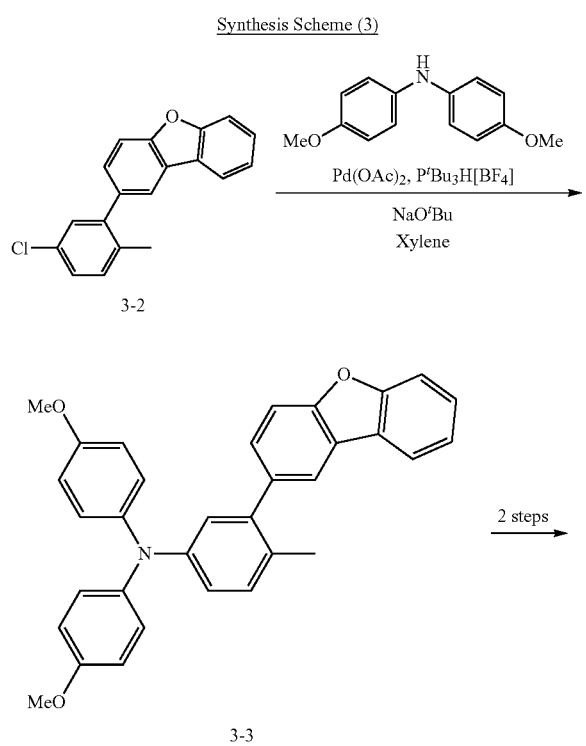

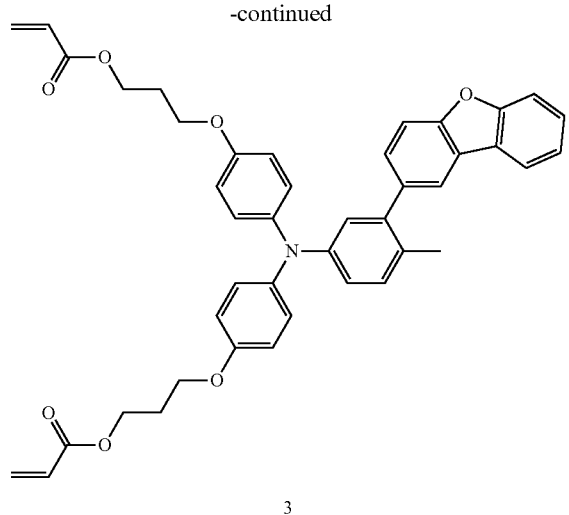

Synthesis of Compound 3-2

The procedure for preparing the compound 1-2 was repeated except for replacing 9-bromophenanthrene with 2-bromodibenzofuran. Thus, a compound 3-2 was prepared.

The compound 3-2 was identified by a nuclear magnetic resonance spectrometer $^1$H-NMR (product of JEOL Ltd., 500 MHz) and a mass spectrometer (LCT-Premier with ASAP Probe, product of Waters Corporation). As a result, it was confirmed from the identified structure and molecular weight that the obtained compound was the objective compound 3-2.

Synthesis of Compound 3-3

The procedure for preparing the compound 1-3 was repeated except for replacing the compound 1-2 with the compound 3-2. Thus, a compound 3-3, that was a colorless amorphous body, was prepared (yield: 2.5 g, 58.5%).

The compound 3-3 was identified by a nuclear magnetic resonance spectrometer $^1$H-NMR (product of JEOL Ltd., 500 MHz) and a mass spectrometer (LCT-Premier with ASAP Probe, product of Waters Corporation). As a result, it was confirmed from the identified structure and molecular weight that the obtained compound was the objective compound 3-3.

Synthesis of Compound 3

The procedure for preparing the compound 1 was repeated except for replacing the compound 1-3 with the compound 3-3. Thus, a compound 3, that was a colorless viscous oil, was prepared (yield: 2.9 g, 92.0%).

The compound 3 was identified by a nuclear magnetic resonance spectrometer $^1$H-NMR (product of JEOL Ltd., 500 MHz) and a mass spectrometer (LCT-Premier with ASAP Probe, product of Waters Corporation). As a result, it was confirmed from the identified structure and molecular weight that the obtained compound was the objective compound 3.

Synthesis Example 4

Synthesis of Electrochromic Compound 4

An electrochromic compound 4 was synthesized according to the following synthesis scheme (4).

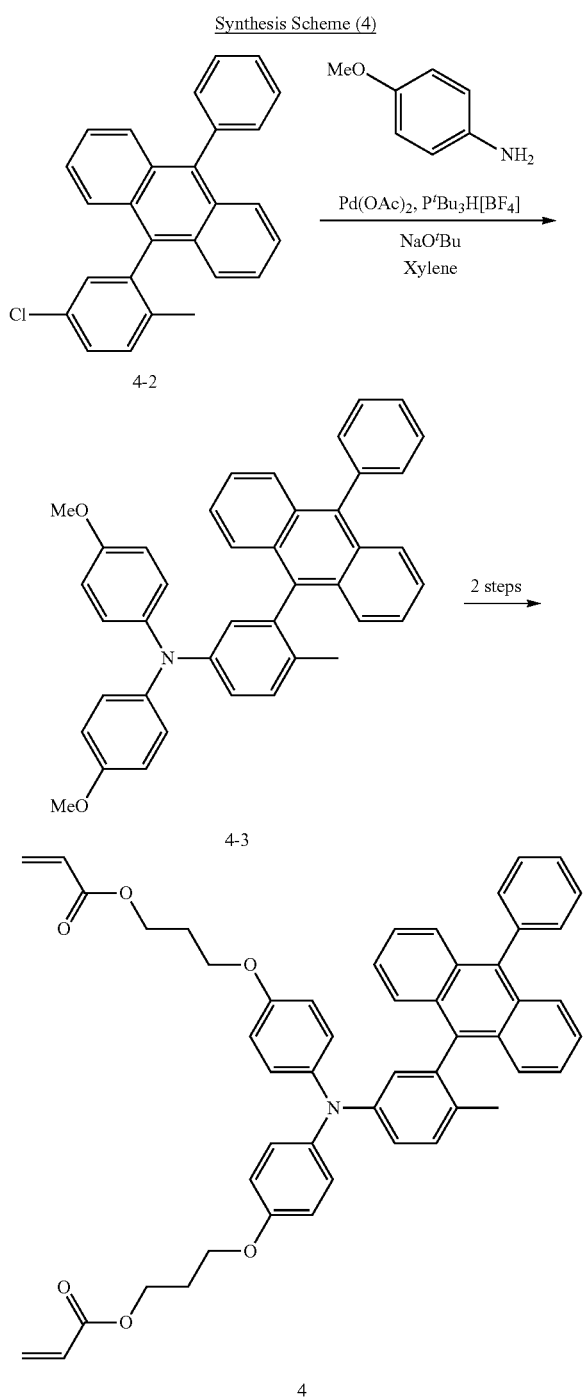

Synthesis of Compound 4-2

The procedure for preparing the compound 1-2 was repeated except for replacing 9-bromophenanthrene with 9-bromo-10-phenylanthracene. Thus, a compound 4-2 was prepared.

The compound 4-2 was identified by a nuclear magnetic resonance spectrometer $^1$H-NMR (product of JEOL Ltd., 500 MHz) and a mass spectrometer (LCT-Premier with ASAP Probe, product of Waters Corporation). As a result, it was confirmed from the identified structure and molecular weight that the obtained compound was the objective compound 4-2.

Synthesis of Compound 4-3

The procedure for preparing the compound 1-3 was repeated except for replacing the compound 1-2 with the compound 4-2. Thus, a compound 4-3, that was a colorless amorphous body, was prepared (yield: 3.1 g, 55.5%).

The compound 4-3 was identified by a nuclear magnetic resonance spectrometer $^1$H-NMR (product of JEOL Ltd., 500 MHz) and a mass spectrometer (LCT-Premier with ASAP Probe, product of Waters Corporation). As a result, it was confirmed from the identified structure and molecular weight that the obtained compound was the objective compound 4-3.

Synthesis of Compound 4

The procedure for preparing the compound 1 was repeated except for replacing the compound 1-3 with the compound 4-3. Thus, a compound 4, that was a colorless viscous oil, was prepared (yield: 2.0 g, 88.0%).

The compound 4 was identified by a nuclear magnetic resonance spectrometer $^1$H-NMR (product of JEOL Ltd., 500 MHz) and a mass spectrometer (LCT-Premier with ASAP Probe, product of Waters Corporation). As a result, it was confirmed from the identified structure and molecular weight that the obtained compound was the objective compound 4.

Preparation of Electrochromic Element According to First Embodiment

Example 1-1

An electrochromic element of Example 1-1 was prepared as follows.

Formation of First Electrochromic Layer on First Electrode

To form a first electrochromic layer on a first electrode, a first electrochromic composition containing the following materials was prepared.

Materials

Electrochromic compound having acryloxy group (Example Compound 1): 50 parts by mass IRGACURE 184 (available from BASF Japan Ltd.): 5 parts by mass Polyethylene glycol having monoacryloxy group (BLEMMER® PME400 available from NOF CORPORATION): 50 parts by mass Methyl ethyl ketone: 900 parts by mass An ITO glass substrate (having an area of 40 mm×40 mm, a thickness of 0.7 mm, and an ITO film thickness of about 100 nm), serving as a first electrode, was coated with the first electrochromic composition by spin coating. The coating layer was exposed to ultraviolet ray emitted from an UV emitter (SPOT CURE available from Ushio Inc.) at 10 mW for 60 seconds, and then subjected to an annealing treatment at 60° C. for 10 minutes. Thus, a first cross-linked electrochromic layer having an average thickness of 400 μm was formed.

Formation of Anti-Deterioration Layer on Second Electrode

Another ITO glass substrate (having an area of 40 mm×40 mm, a thickness of 0.7 mm, and an ITO film thickness of about 100 nm), serving as a second electrode, was coated with a titanium oxide nanoparticle dispersion liquid (SP210 available from Showa Titanium Co., Ltd., having an average particle diameter of about 20 nm) by spin coating, to form an anti-deterioration layer. The coating layer was subjected to an annealing treatment at 120° C. for 15 minutes. Thus, a nanostructural semiconductive material comprising a titanium oxide particle film having a thickness of 1.0 μm was formed.

Formation of Second Electrochromic Layer on Second Electrode

To form a second electrochromic layer on a second electrode, a second electrochromic composition containing the following materials was prepared.

Materials

Electrochromic compound having a functional group bindable to hydroxyl group (Example Compound A): 20 parts by mass Tetrafluoropropanol: 980 parts by mass The nanostructural semiconductive material comprising a titanium oxide particle film, formed on the second electrode, was then coated and adsorbed with the second electrochromic composition by spin coating. Non-adsorbed compounds were washed with methanol. Thus, a second electrochromic layer was formed.

Filling of Electrolyte Liquid

An electrolyte liquid containing the following materials was prepared.

Materials

IRGACURE 184 (available from BASF Japan Ltd.): 5 parts by mass

PEG400DA (available from Nippon Kayaku Co., Ltd.): 100 parts by mass

1-Ethyl-3-methylimidazolium tetracyanoborate (available from Merk KGaA): 50 parts by mass The above-prepared electrolyte liquid in an amount of 30 mg was weighed with a micro pipette and dropped onto the ITO glass substrate serving as the second electrode having the anti-deterioration layer and the second electrochromic layer thereon. The ITO glass substrate serving as the first electrode having the first cross-linked electrochromic layer thereon was bonded to the above ITO glass substrate serving as the second electrode while forming extracted portions, thus forming a bonded element. The bonded element was exposed to ultraviolet light (having a wavelength of 250 nm) emitted from a UV emitter (SPOT CURE available from Ushio Inc.) at 10 mW for 60 seconds. Thus, an electrochromic element of Example 1-1 was prepared.

Coloring-Bleaching Drive Operation

Figure 3:
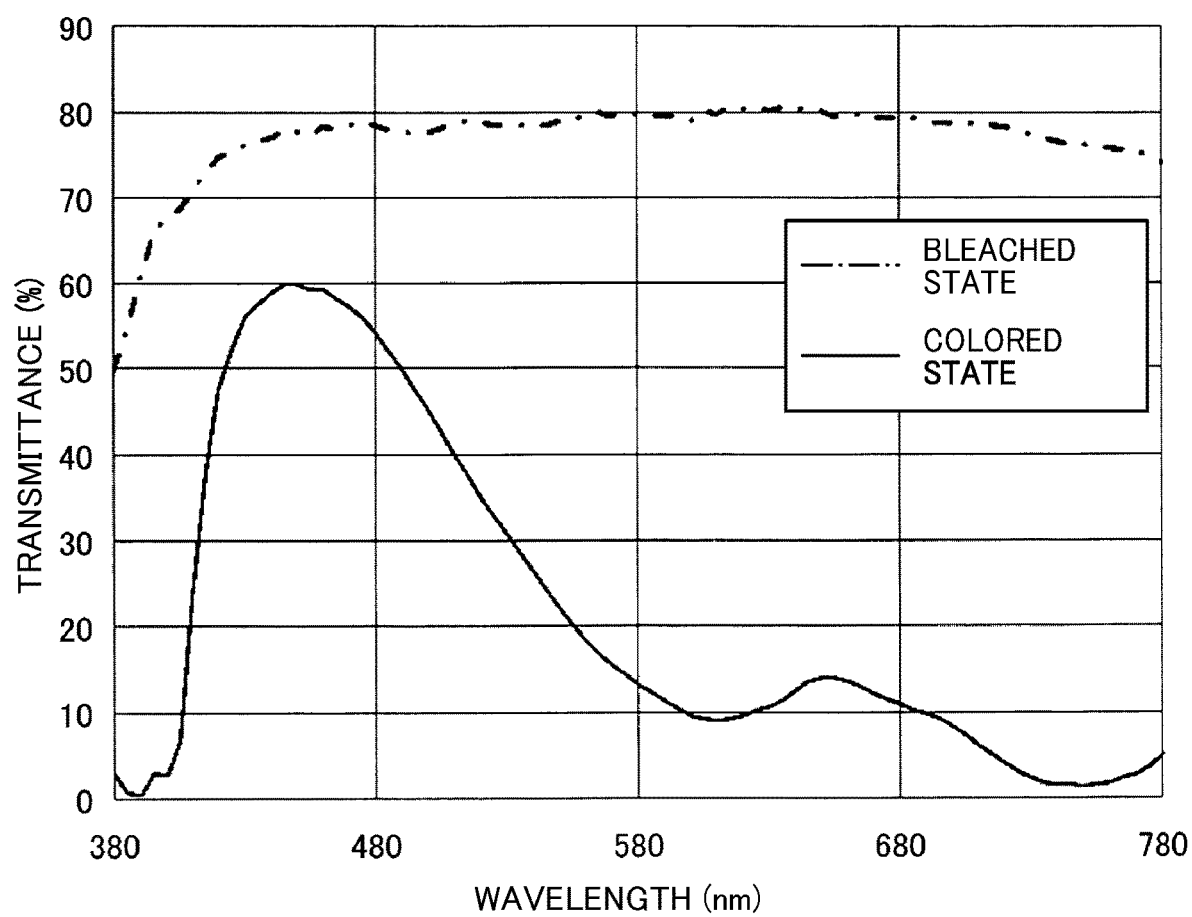
FIG. 3 is a graph showing a transmission spectrum of an electrochromic element of Example 1-1 in bleached and colored states.

Coloring and bleaching of the electrochromic element of Example 1-1 were confirmed as follows. The results are shown in FIG. 3. A voltage of −2 V was applied for 5 seconds to between the extracted portions of the first electrode and the second electrode. As a result, it was confirmed that the color derived from the electrochromic compound (Example Compound 1) in the first electrochromic layer was developed at the portion where the first electrode and the second electrode were overlapped. In addition, it was confirmed that the color derived from the electrochromic compound (Example Compound A) in the second electrochromic layer was developed. Next, a voltage of +2 V was applied for 5 seconds to between the extracted portions of the first electrode and the second electrode. As a result, the portion where the first electrode and the second electrode were overlapped was bleached and became transparent.

Examples 1-2 to 1-20

The procedure in Example 1-1 was repeated except for replacing the electrochromic compound (Example Compound 1) with each of Example Compounds 2 to 20.

Comparative Examples 1-1 to 1-5

The procedure in Example 1-1 was repeated except for replacing the electrochromic compound (Example Compound 1) with each of the following Comparative Compounds 1 to 5.

Comparative Compound 1

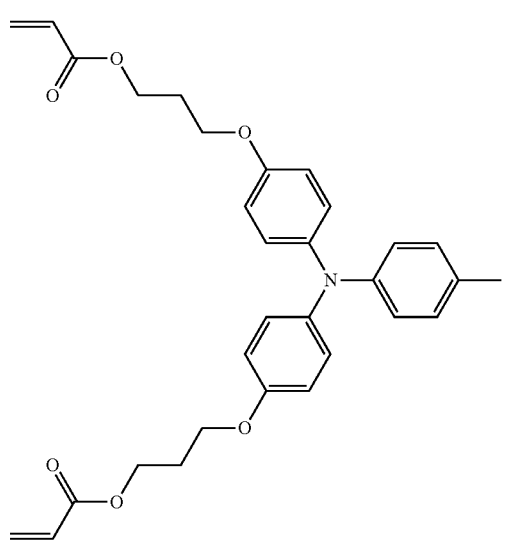

Comparative Compound 2
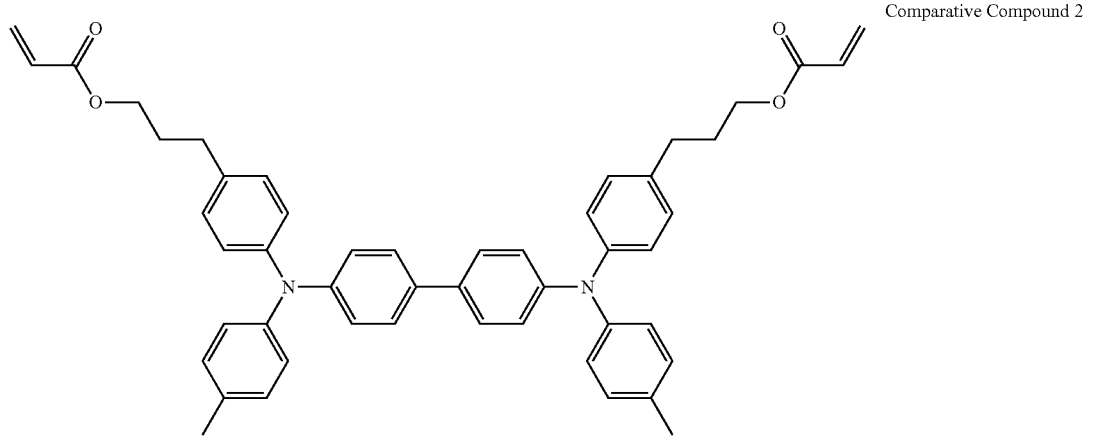
Comparative Compound 3
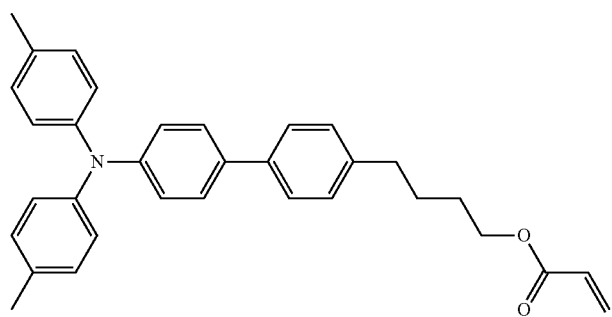
Comparative Compound 4
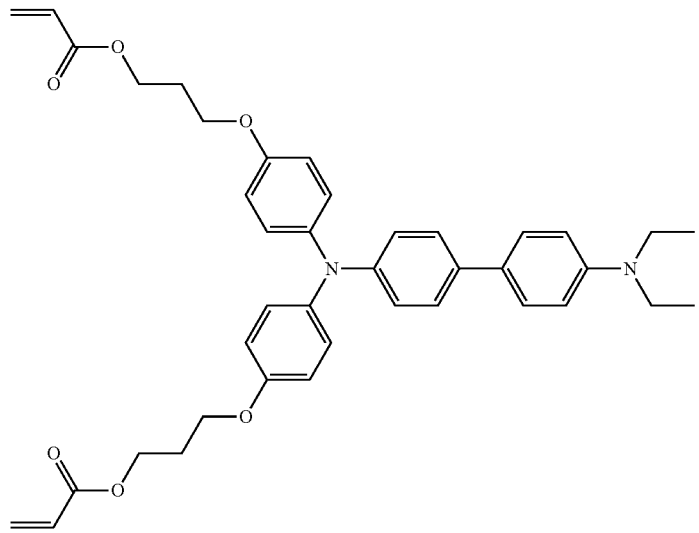

-continued
Comparative Compound 5

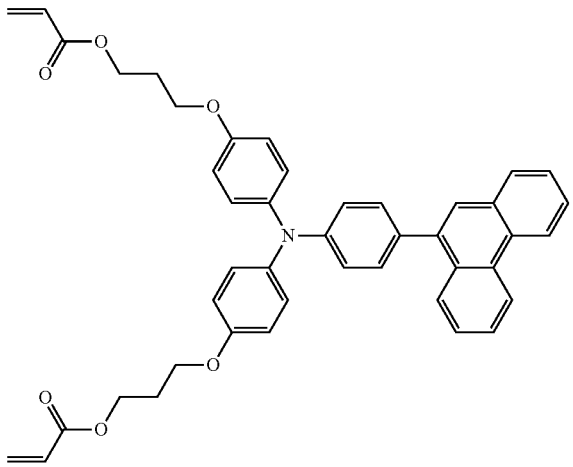

The type and application position of electrochromic compounds in each Examples and Comparative Examples are shown in Table 1.

Evaluations

Each electrochromic element was subjected to a repetition durability test, a continuous coloring test, a light durability test, and a color test as follows.

Test 1-1: Repetition Durability Test

Each electrochromic element prepared in Examples and Comparative Examples was subjected to a coloring-bleaching drive operation, in which a voltage of −2 V was applied for 5 seconds and thereafter a voltage of +2 V for 5 seconds to between the extracted portions of the first electrode and the second electrode, for 10,000 times. A wavelength λmax at which the absorbance became a local maximum was determined within a visible range (400 to 800 nm). (λmax was 700 nm in Example 1.) Repetition durability was evaluated by the change in absorbance at λmax, measured with a spectrometer USB4000, based on the following criteria. The results are shown in Table 1.

Evaluation Criteria

A+: Absorbance at λmax was 90% or more of the initial absorbance.

A: Absorbance at λmax was 80% or more of the initial absorbance.

B: Absorbance at λmax was 50% or more of the initial absorbance.

C: Absorbance at λmax was less than 50% of the initial absorbance.

Test 1-2: Continuous Coloring Test

In each electrochromic element prepared in Examples and Comparative Examples, a voltage of 1.6 V was applied to between the first electrode and the second electrode, and the electrochromic element was maintained in a colored state for continuous 48 hours. The absorbance within a visible range (380 to 800 nm) was measured with a spectrometer USB4000 and a yellow index (YI) was calculated before and after the application of voltage. Continuous coloring property was evaluated by the difference in yellow index (ΔYI) before and after the application of voltage based on the following criteria. The results are shown in Table 1.

Evaluation Criteria

A+: ΔYI was less than 1.

A: ΔYI was 1 or greater but less than 5.

B: ΔYI was 5 or greater but less than 10.

C: ΔYI was 10 or greater.

Test 1-3: Light Durability Test

In each electrochromic element prepared in Examples and Comparative Examples, a voltage of 1.6 V was applied to between the first electrode and the second electrode. While maintaining the electrochromic element in a colored state, the electrochromic element was irradiated with light emitted from an artificial solar lighting (SOLAX XC-100W available from SERIC Ltd., having an illuminance of 150,000 lux) through an ultraviolet cut filter (LUMICOOL 1501UH available from LINTEC Corporation) for continuous 48 hours. The electrochromic element was further irradiated with light emitted from a deuterium tungsten halogen light source (DH-2000 available from Ocean Optics, Inc.), and the transmitted light was detected by a spectrometer USB4000 to obtain a transmission spectrum. A wavelength λmax at which the transmittance became the minimum was determined within a visible range (400 to 800 nm). Light durability was evaluated by the transmittance at λmax based on the following criteria. The results are shown in Table 1.

Evaluation Criteria

A+: Transmittance at λmax was less than 10%.

A: Transmittance at λmax was 10% or greater but less than 30%.

B: Transmittance at λmax was 30% or greater.

C: Transmittance at λmax was 50% or greater.

Test 1-4: Color Test

In each electrochromic element prepared in Examples and Comparative Examples, a voltage of −2 V was applied for 5 seconds to cause coloring of the electrochromic element. A wavelength λmax at which the absorbance became a local maximum was determined within a visible range (400 to 800 nm). (λmax was 700 nm in Example 1-1.) The change in absorbance at λmax was measured with a spectrometer USB4000. After subtracting the spectrum of the electrochromic element in the second electrochromic layer, the color was visually observed and evaluated based on the following criteria. The results are shown in Table 1.

Evaluation Criteria

A: The visually observed color was blue.

C: The visually observed color was other than blue.

TABLE 1

| Examples | Electrochromic Compound in First Electrochromic Layer | Electrochromic Compound in Second Electrochromic Layer | Test 1-1 | Test 1-2 | Test 1-3 | Test 1-4 |
|---|---|---|---|---|---|---|
| Example 1-1 | Example Compound 1 | Example Compound A | A+ | A+ | A+ | A |
| Example 1-2 | Example Compound 2 | Example Compound A | A+ | A+ | A+ | A |
| Example 1-3 | Example Compound 3 | Example Compound A | A+ | A+ | A+ | A |
| Example 1-4 | Example Compound 4 | Example Compound A | A+ | A+ | A+ | A |
| Example 1-5 | Example Compound 5 | Example Compound A | A+ | A+ | A+ | A |
| Example 1-6 | Example Compound 6 | Example Compound A | A+ | A+ | A+ | A |
| Example 1-7 | Example Compound 7 | Example Compound A | A+ | A+ | A+ | A |
| Example 1-8 | Example Compound 8 | Example Compound A | A+ | A+ | A+ | A |
| Example 1-9 | Example Compound 9 | Example Compound A | A+ | A+ | A+ | A |
| Example 1-10 | Example Compound 10 | Example Compound A | A+ | A+ | A+ | A |
| Example 1-11 | Example Compound 11 | Example Compound A | A+ | A+ | A+ | A |
| Example 1-12 | Example Compound 12 | Example Compound A | A+ | A+ | A+ | A |
| Example 1-13 | Example Compound 13 | Example Compound A | A+ | A+ | A+ | A |
| Example 1-14 | Example Compound 14 | Example Compound A | A+ | A+ | A+ | A |
| Example 1-15 | Example Compound 15 | Example Compound A | A+ | A+ | A+ | A |
| Example 1-16 | Example Compound 16 | Example Compound A | A+ | A+ | A+ | A |
| Example 1-17 | Example Compound 17 | Example Compound A | A+ | A+ | A+ | A |
| Example 1-18 | Example Compound 18 | Example Compound A | A+ | A+ | A+ | A |
| Example 1-19 | Example Compound 19 | Example Compound A | A+ | A+ | A+ | A |
| Example 1-20 | Example Compound 20 | Example Compound A | A+ | A+ | A+ | A |
| Comparative Example 1-1 | Comparative Compound 1 | Example Compound A | A+ | A | C | C |
| Comparative Example 1-2 | Comparative Compound 2 | Example Compound A | A+ | A+ | A+ | C |
| Comparative Example 1-3 | Comparative Compound 3 | Example Compound A | A+ | A | C | C |
| Comparative Example 1-4 | Comparative Compound 4 | Example Compound A | A | B | C | C |
| Comparative Example 1-5 | Comparative Compound 5 | Example Compound A | A | A | B | C |

It is clear from Table 1 that the electrochromic elements according to the first embodiment deliver satisfactory repetition durability, continuous coloring property, light durability, and color. In particular, continuous driving stability and light durability are excellent. By contrast, comparative electrochromic elements are insufficient in at least one of light durability and color.

Preparation of Electrochromic Element According to Second Embodiment

Example 2-1

An electrochromic element of Example 2-1 was prepared as follows.

Formation of Spacer on First Electrode

An ITO glass substrate (having an area of 40 mm×40 mm, a thickness of 0.7 mm, and an ITO film thickness of about 100 nm), serving as a first electrode, was coated with an isopropanol solution of gap control particles (MICROPEARL GS available from Sekisui Chemical Co., Ltd., having a particle diameter of 80 μm) and dried at 80° C. for 3 minutes.

Formation of Anti-Deterioration Layer on Second Electrode

Another ITO glass substrate (having an area of 40 mm×40 mm, a thickness of 0.7 mm, and an ITO film thickness of about 100 nm), serving as a second electrode, was coated with a titanium oxide nanoparticle dispersion liquid (SP210 available from Showa Titanium Co., Ltd., having an average particle diameter of about 20 nm) by spin coating, to form an anti-deterioration layer. The coating layer was subjected to an annealing treatment at 120° C. for 15 minutes. Thus, a nanostructural semiconductive material comprising a titanium oxide particle film having a thickness of 1.0 μm was formed.

Bonding of Substrates

The ITO substrate as the first electrode and the ITO substrate as the second electrode were bonded to each other with the electrode surfaces facing each other and shifted 5 mm to form extracted portions. The end faces of the bonded substrates were coated with a sealing material (TB 3050B available from ThreeBond Group) while leaving two injection holes. The bonded element was irradiated with ultraviolet light (having a wavelength of 250 nm) emitted from a UV emitter (SPOT CURE available from Ushio Inc.) at 10 mW for 60 seconds.

Filling of Electrolyte Liquid

An electrolyte liquid containing the following materials was prepared.

Materials

Electrochromic compound (Example Compound M1): 50 parts by mass

EMIM-FSI (available from Merk KGaA): 100 parts by mass

Propylene carbonate: 600 parts by mass

The above-prepared electrolyte liquid in an amount of 30 mg was weighed with a micro pipette and injected into the element from the injection holes. The injection holes were sealed with the sealing material and exposed to ultraviolet light (having a wavelength of 250 nm) emitted from a UV emitter (SPOT CURE available from Ushio Inc.) at 10 mW for 60 seconds. Thus, an electrochromic element of Example 2-1, illustrated in FIG. 2, was prepared.

Coloring-Bleaching Drive Operation

Coloring and bleaching of the electrochromic element of Example 2-1 were confirmed in the same manner as the electrochromic element of Example 1-1. As a result, it was confirmed that, when a voltage of −2 V was applied for 5 seconds to between the extracted portions of the first electrode and the second electrode, the color derived from the electrochromic compound was developed at the portion where the first electrode and the second electrode were overlapped. In was also confirmed that, when a voltage of +2 V was applied for 5 seconds to between the extracted portions of the first electrode and the second electrode thereafter, the portion where the first electrode and the second electrode were overlapped was bleached and became transparent.

Examples 2-2 and 2-3

The procedure in Example 2-1 was repeated except for replacing the Example Compound M1 with each of Example Compounds M2 and M3.

Comparative Examples 2-1 to 2-5

The procedure in Example 2-1 was repeated except for replacing the Example Compound M1 with each of the following Comparative Compounds m1 to m5.

Comparative Compound m1

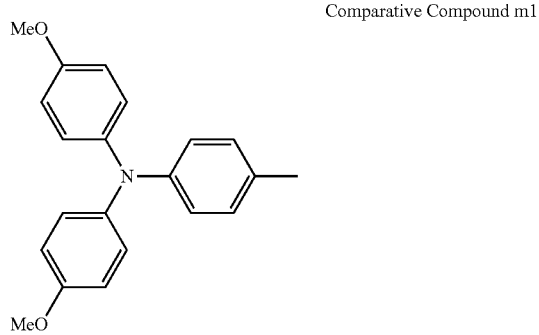

Comparative Compound m2

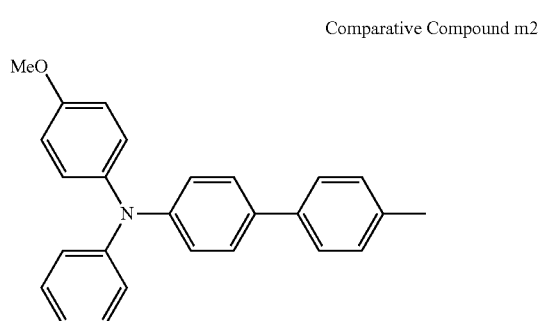

Comparative Compound m3

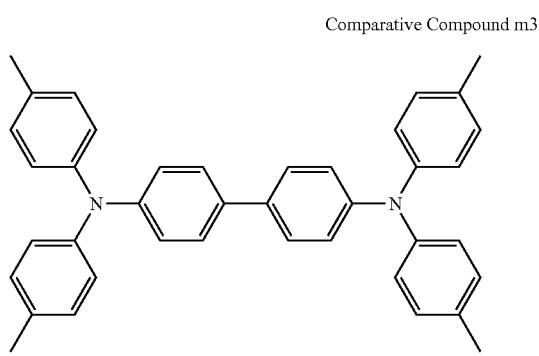

Comparative Compound m4

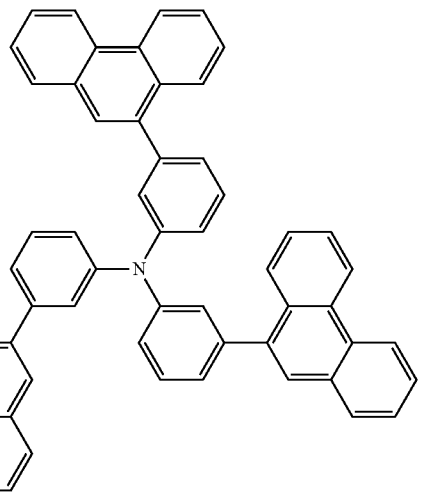

Comparative Compound m5

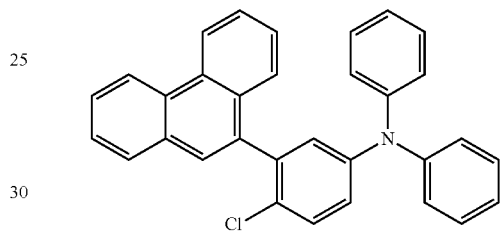

Evaluations

Each electrochromic element was subjected to a continuous coloring test, a light durability test, a color test, and a degraded material analysis as follows.

Test 2-1: Continuous Coloring Test

In each electrochromic element prepared in Examples and Comparative Examples, a voltage of 1.6 V was applied to between the first electrode and the second electrode, and the electrochromic element was maintained in a colored state for continuous 48 hours. The absorbance within a visible range (380 to 800 nm) was measured with a spectrometer USB4000 and a yellow index (YI) was calculated before and after the application of voltage. Continuous coloring property was evaluated by the difference in yellow index (ΔYI) before and after the application of voltage based on the following criteria. The results are shown in Table 2.

Evaluation Criteria

A+: ΔYI was less than 1.
A: ΔYI was 1 or greater but less than 5.
B: ΔYI was 5 or greater but less than 10.
C: ΔYI was 10 or greater.

Test 2-2: Light Durability Test

Each electrochromic element prepared in Examples and Comparative Examples was subjected to a light durability test conducted in the same manner as Test 1-3 described above. The results are shown in Table 2.

Test 2-3: Color Test

Each electrochromic element prepared in Examples and Comparative Examples was subjected to a color test conducted in the same manner as Test 1-4 described above. The results are shown in Table 2.

Test 2-4: Deteriorated Matter Analysis

After the Test 2-2, the sealing material of the electrochromic element was cut to take out the electrolyte liquid from the inside. The electrolyte liquid was dissolved in MeCN and analyzed by a liquid chromatography mass spectrometry (LC/MS) instrument (HPLC Alliance/TOF-MS LCT-Premier available from Waters Corporation). Cyclized matters were detected by a photodiode detector (200 to 800 nm) and a mass spectrometer (APCI mode) and quantified by calculating the area ratio between them and the main component under the absorbance spectrum at 300 nm. The analysis results were evaluated based on the following criteria. The results are shown in Table 2.

Analysis Conditions

Column: Super ODS (an inner diameter of 4.6 mm×100 mm, available from Tosoh Corporation)

Solvent: Mixed solvent of acetonitrile and water (the ratio of acetonitrile:water was changed from 50:50 to 100:0 with a linear gradient) within a time period of from 0 to 10 minutes, and 100% acetonitrile within a time period of from 10 to 15 minutes.

Evaluation Criteria

A: The generation rate of cyclized matters was less than 1%.

C: The generation rate of cyclized matters was 1% or greater.

TABLE 2

| Examples | Electrochromic Compound in Electrolyte Layer | Test 2-1 | Test 2-2 | Test 2-3 | Test 2-4 |
|---|---|---|---|---|---|
| Example 2-1 | Example Compound M1 | A+ | A+ | A | A |
| Example 2-2 | Example Compound M2 | A+ | A+ | A | A |
| Example 2-3 | Example Compound M3 | A+ | A+ | A | A |
| Comparative Example 2-1 | Comparative Compound m1 | A | C | B | C |
| Comparative Example 2-2 | Comparative Compound m2 | B | C | B | C |
| Comparative Example 2-3 | Comparative Compound m3 | A | A+ | B | A |
| Comparative Example 2-4 | Comparative Compound m4 | B | A | B | A |
| Comparative Example 2-5 | Comparative Compound m5 | B | A | B | A |

It is clear from Table 2 that the electrochromic elements according to the second embodiment develop blue color while providing excellent continuous driving stability and light durability. By contrast, comparative electrochromic elements are insufficient in at least one of light durability and blue color developing property. In addition, it was confirmed that the electrochromic compound used in the second embodiment generates very few cyclized bodies (carbazole derivatives), i.e., byproducts produced by light irradiation, that degrade electrochromic elements. Thus, the electrochromic compound used in the second embodiment contributes to improvement of light durability of the electrochromic element.

Numerous additional modifications and variations are possible in light of the above teachings. It is therefore to be understood that, within the scope of the above teachings, the present disclosure may be practiced otherwise than as specifically described herein. With some embodiments having thus been described, it will be obvious that the same may be varied in many ways. Such variations are not to be regarded as a departure from the scope of the present disclosure and appended claims, and all such modifications are intended to be included within the scope of the present disclosure and appended claims.

The invention claimed is:

1. An electrochromic compound represented by formula (1):

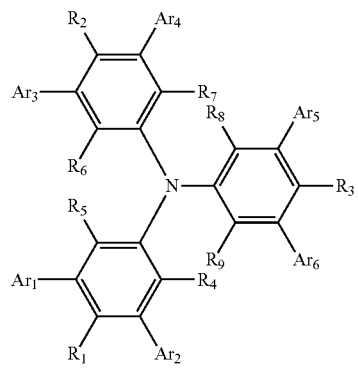

Formula (1)

where each of $R_1$ to $R_9$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

each of $Ar_1$ to $Ar_6$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

at least one of $Ar_1$ to $Ar_6$ represents an aryl group, a heteroaryl group, or a group selected from the group consisting of

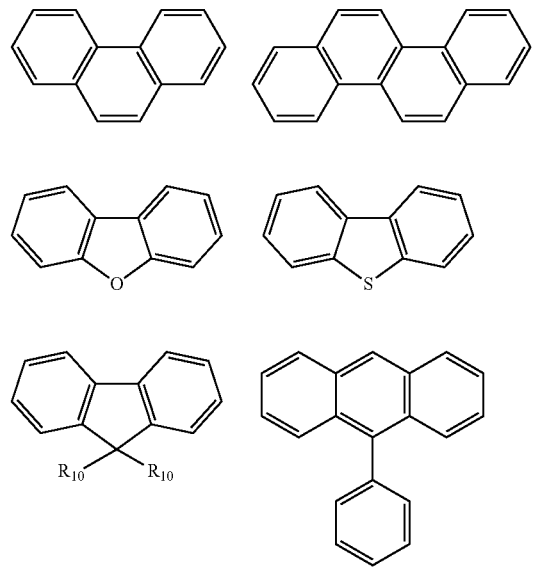

-continued

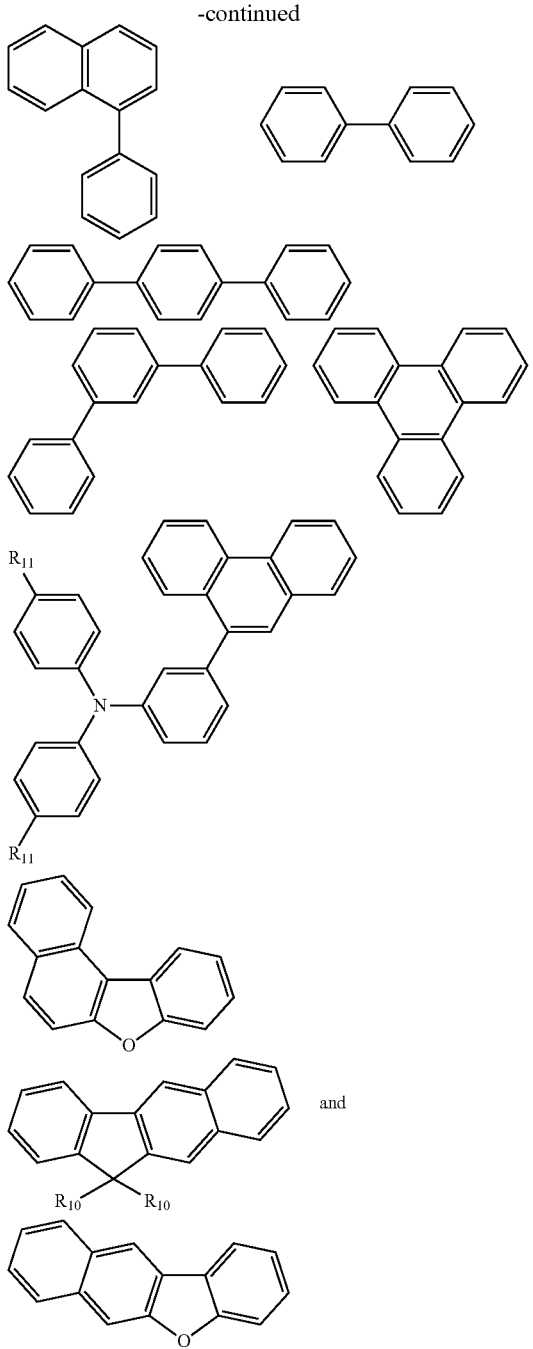

among Ar₁ to Ar₆, no more than one group attached to the same aryl group of the formula (1) is a group in which at least two aryl groups are condensed with each other to form a ring; and wherein the total number of aromatic rings and heterocyclic rings constituting each of Ar₁ to Ar₆ is 2 or more where the aromatic rings and heterocyclic rings are either condensed with each other or directly bonded to each other via covalent bonds and the heterocyclic rings do not include a nitrogen atom.

2. The electrochromic compound of claim 1, wherein at least one of R₁ to R₉ represents a polymerizable functional group.

3. The electrochromic compound of claim 1, wherein each of R₁ to R₉ independently represents an alkyl group, an alkoxy group, or a polymerizable functional group.

4. The electrochromic compound of claim 1, wherein each of R₁ to R₃ independently represents an alkyl group, an alkenyl group, an alkynyl group, or an alkoxy group.

5. The electrochromic compound of claim 1, wherein
at least one of R₁ to R₉ and/or at least one of Ar₁ to Ar₆ is independently a group in which two or more aryl and/or heteroaryl groups are bound to each other via a covalent bond, or a group in which two or more aryl and/or heteroaryl groups are condensed with each other to form a ring; and
the group in which two or more aryl and/or heteroaryl groups are bound to each other via a covalent bond and the group in which two or more aryl and/or heteroaryl groups are condensed with each other to form a ring each contain 1 to 36 carbon atoms.

6. The electrochromic compound of claim 5, wherein the group in which two or more aryl and/or heteroaryl groups are bound to each other via a covalent bond and the group in which two or more aryl and/or heteroaryl groups are condensed with each other to form a ring each further contain a hetero atom.

7. The electrochromic compound of claim 1, wherein
at least one of R₁ to R₉ and/or at least one of Ar₁ to Ar₆ is independently a group in which two or more aryl and/or heteroaryl groups are bound to each other via a covalent bond, or a group in which two or more aryl and/or heteroaryl groups are condensed with each other to form a ring; and
the group in which two or more aryl and/or heteroaryl groups are bound to each other via a covalent bond and the group in which two or more aryl and/or heteroaryl groups are condensed with each other to form a ring each represent a group obtained by removing a hydrogen atom from an arbitrary carbon atom on an outer edge of a molecule of one of the following compounds:

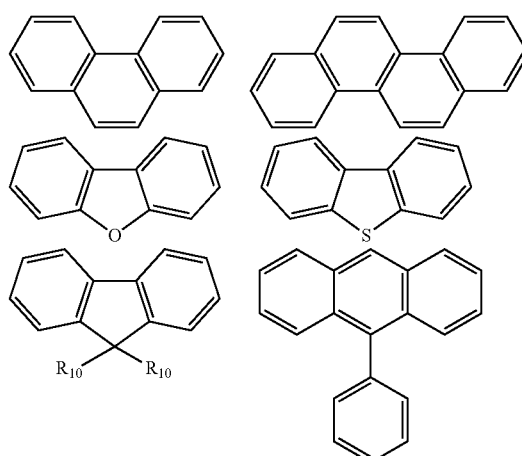

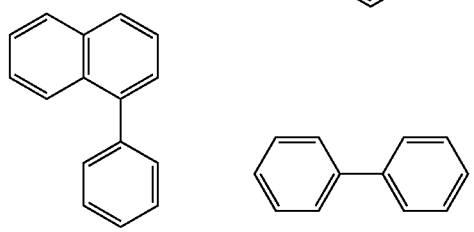

-continued

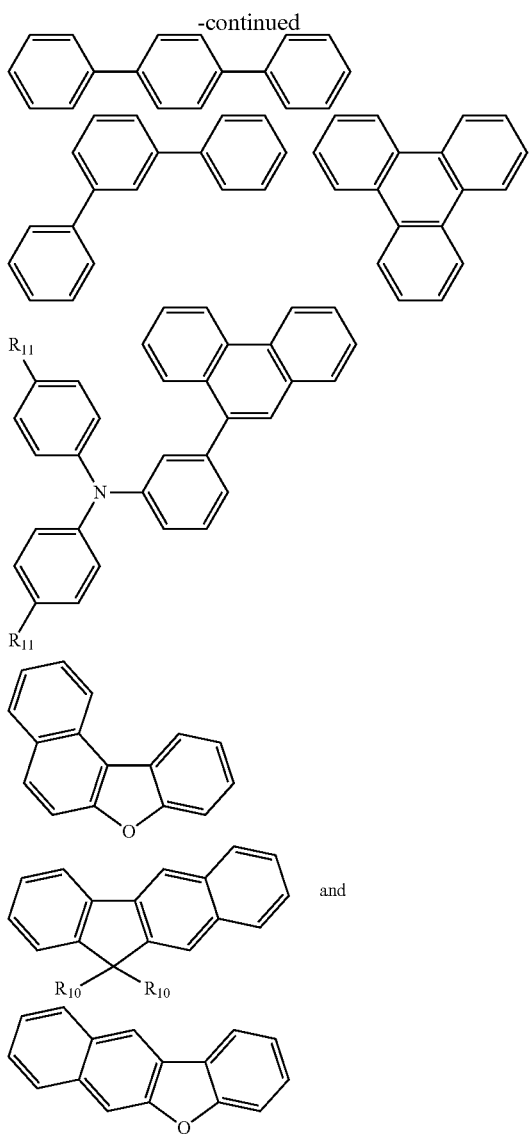

where each of $R_{10}$ and $R_{12}$ independently represents an alkyl group or an aryl group and $R_{11}$ represents an alkyl group, an alkenyl group, or an alkoxy group.

8. An electrochromic composition, comprising:
the electrochromic compound of claim 1; and
a radical polymerizable compound.

9. An electrochromic element, comprising:
a first electrode;
an electrochromic layer on the first electrode, the electrochromic layer containing the electrochromic compound of claim 1;
a second electrode facing the first electrode with a gap therebetween; and
an electrolyte layer disposed between the first electrode and the second electrode.

10. An electrochromic element, comprising:
a first electrode;
a second electrode facing the first electrode with a gap therebetween; and
an electrolyte layer disposed between the first electrode and the second electrode, the electrolyte layer containing the electrochromic compound of claim 1.

11. The electrochromic compound of claim 1, wherein among $Ar_1$ to $Ar_6$, no more than one group attached to the same aryl group of the formula (1) is an aryl group.

12. The electrochromic compound of claim 1, wherein among $Ar_1$ to $Ar_6$, no more than one group attached to the same aryl group of the formula (1) is a heteroaryl group.

13. The electrochromic compound of claim 1, wherein among $Ar_1$ to $Ar_6$, no more than one group attached to the same aryl group of the formula (1) is a group in which two or more aryl and/or heteroaryl groups are bound to each other via a covalent bond.

14. The electrochromic compound of claim 1, wherein among $Ar_1$ to $Ar_6$, no more than one group attached to the same aryl group of the formula (1) is a group in which at least two heteroaryl groups are condensed with each other to form a ring.

15. An electrochromic compound represented by formula (1):

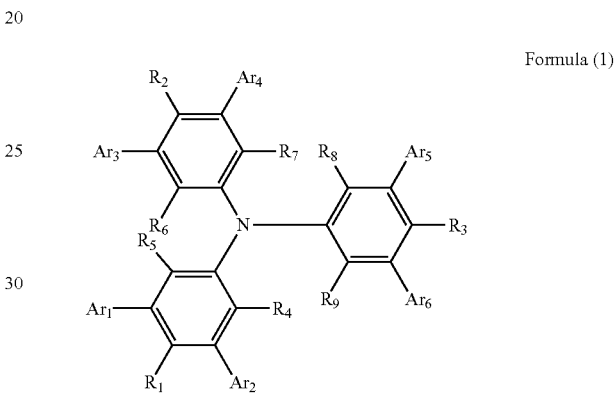

Formula (1)

where each of $R_1$ to $R_9$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group, wherein at least one of $R_1$ to $R_9$ represents a polymerizable functional group;
each of $Ar_1$ to $Ar_6$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;
at least one of $Ar_1$ to $Ar_6$ represents an aryl group, a heteroaryl group, or a group selected from the group consisting of

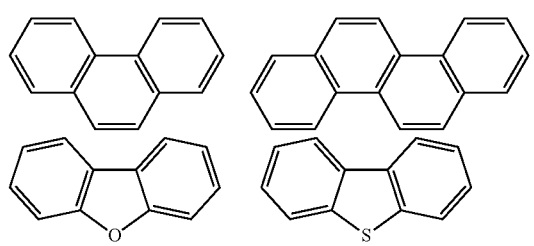

-continued

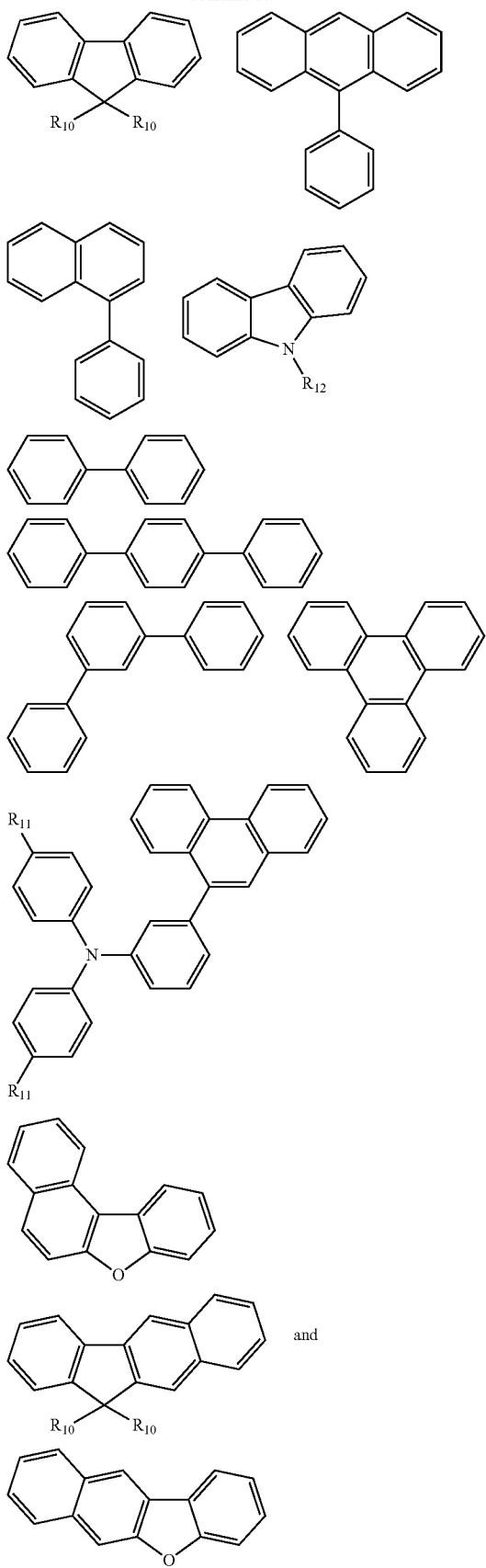

and among $Ar_1$ to $Ar_6$, no more than one group attached to the same aryl group of the formula (1) is a group in which at least two aryl groups are condensed with each other to form a ring.

16. An electrochromic compound represented by formula (1):

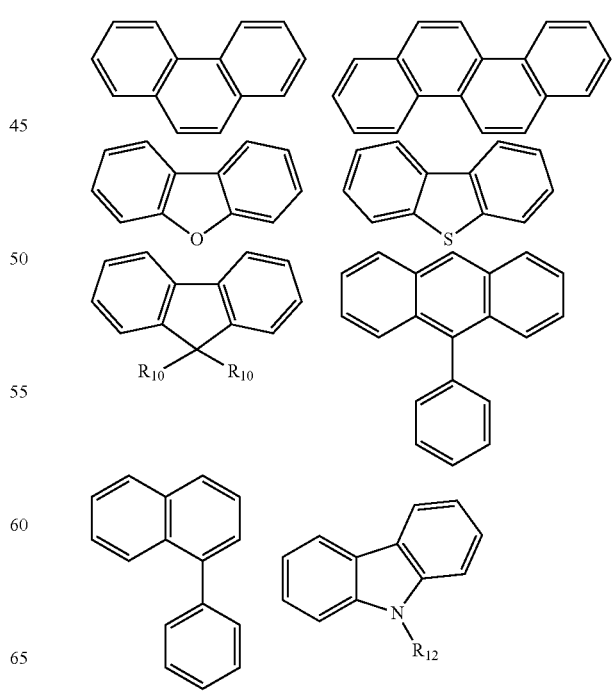

Formula (1)

where each of $R_1$ to $R_9$ independently represents an alkyl group, an alkoxy group, or a polymerizable functional group;

each of $Ar_1$ to $Ar_6$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

at least one of $Ar_1$ to $Ar_6$ represents an aryl group, a heteroaryl group, or a group selected from the group consisting of -continued

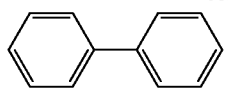

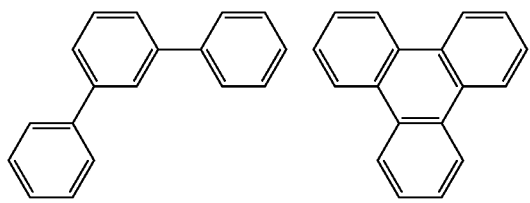

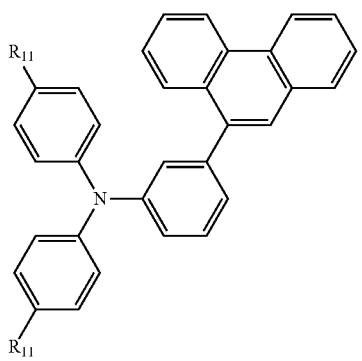

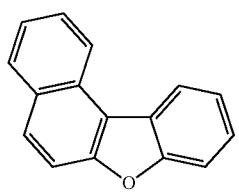

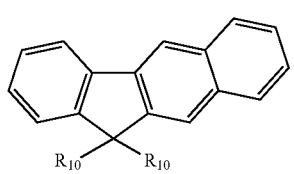

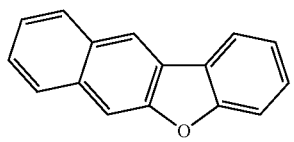

among $Ar_1$ to $Ar_6$, no more than one group attached to the same aryl group of the formula (1) is a group in which at least two aryl groups are condensed with each other to form a ring.

17. An electrochromic compound represented by formula (1):

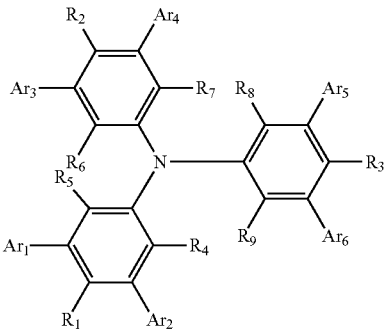

Formula (1)

where each of $R_1$ to $R_3$ independently represents an alkyl group, an alkenyl group, an alkynyl group, or an alkoxy group;

each of $R_4$ to $R_9$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group, wherein at least one of $R_1$ to $R_9$ represents a polymerizable functional group;

each of $Ar_1$ to $Ar_6$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

at least one of $Ar_1$ to $Ar_6$ represents an aryl group, a heteroaryl group, or a group selected from the group consisting of

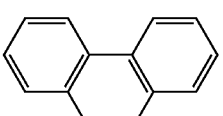 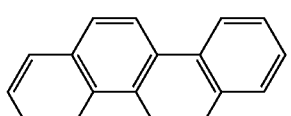

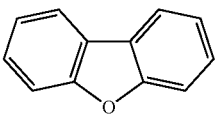 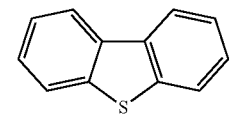

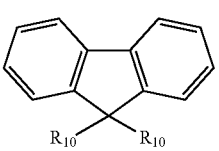 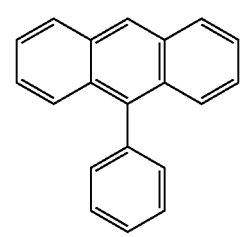

-continued

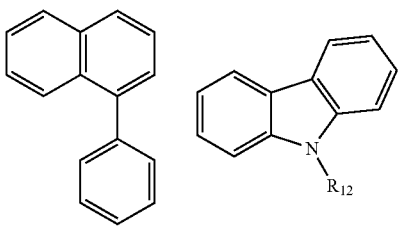

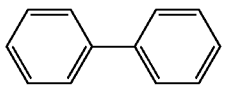

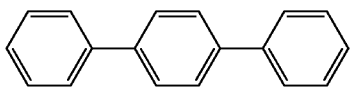

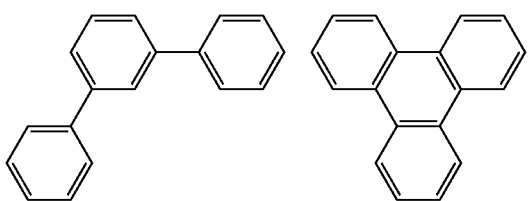

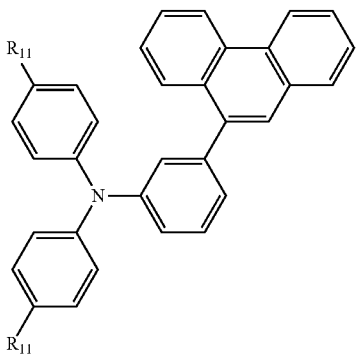

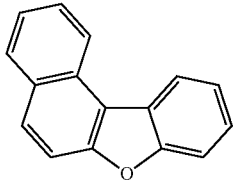

and

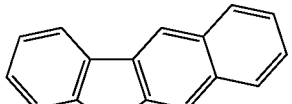

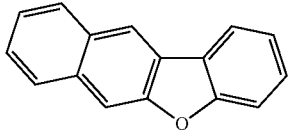

among $Ar_1$ to $Ar_6$, no more than one group attached to the same aryl group of the formula (1) is a group in which at least two aryl groups are condensed with each other to form a ring.

18. An electrochromic compound represented by formula (1):

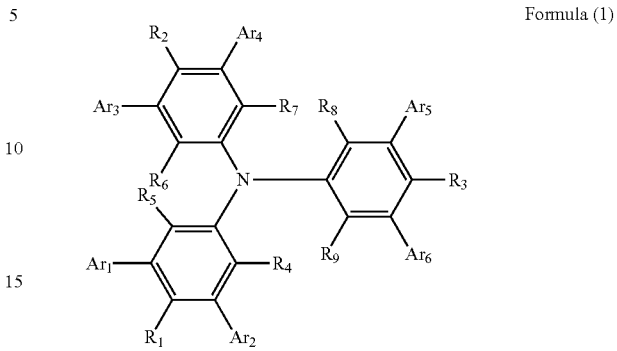

Formula (1)

where each of $R_1$ to $R_9$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

each of $Ar_1$ to $Ar_6$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

at least one of $Ar_1$ to $Ar_6$ represents an aryl group, a heteroaryl group, or a group selected from the group consisting of

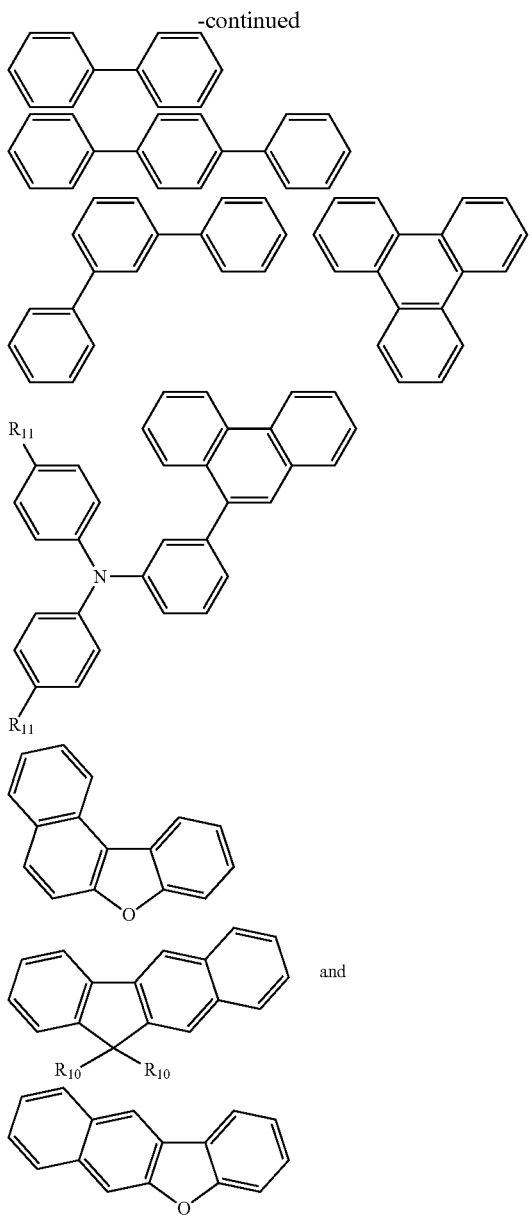

among Ar$_1$ to Ar$_6$, no more than one group attached to the same aryl group of the formula (1) is a group in which at least two aryl groups are condensed with each other to form a ring, and wherein at least one of R$_1$ to R$_9$ and/or at least one of Ar$_1$ to Ar$_6$ is independently a group in which two or more aryl and/or heteroaryl groups are bound to each other via a covalent bond, or a group in which two or more aryl and/or heteroaryl groups are condensed with each other to form a ring; and the group in which two or more aryl and/or heteroaryl groups are bound to each other via a covalent bond and the group in which two or more aryl and/or heteroaryl groups are condensed with each other to form a ring each contain 1 to 36 carbon atoms.

19. The electrochromic compound of claim 18, wherein the group in which two or more aryl and/or heteroaryl groups are bound to each other via a covalent bond and the group in which two or more aryl and/or heteroaryl groups are condensed with each other to form a ring each further contain a hetero atom.

20. The electrochromic compound of claim 18, the group in which two or more aryl and/or heteroaryl groups are bound to each other via a covalent bond and the group in which two or more aryl and/or heteroaryl groups are condensed with each other to form a ring each contain 1 to 36 carbon atoms is a ring each representing a group obtained by removing a hydrogen atom from an arbitrary carbon atom on an outer edge of a molecule of one of the following compounds:

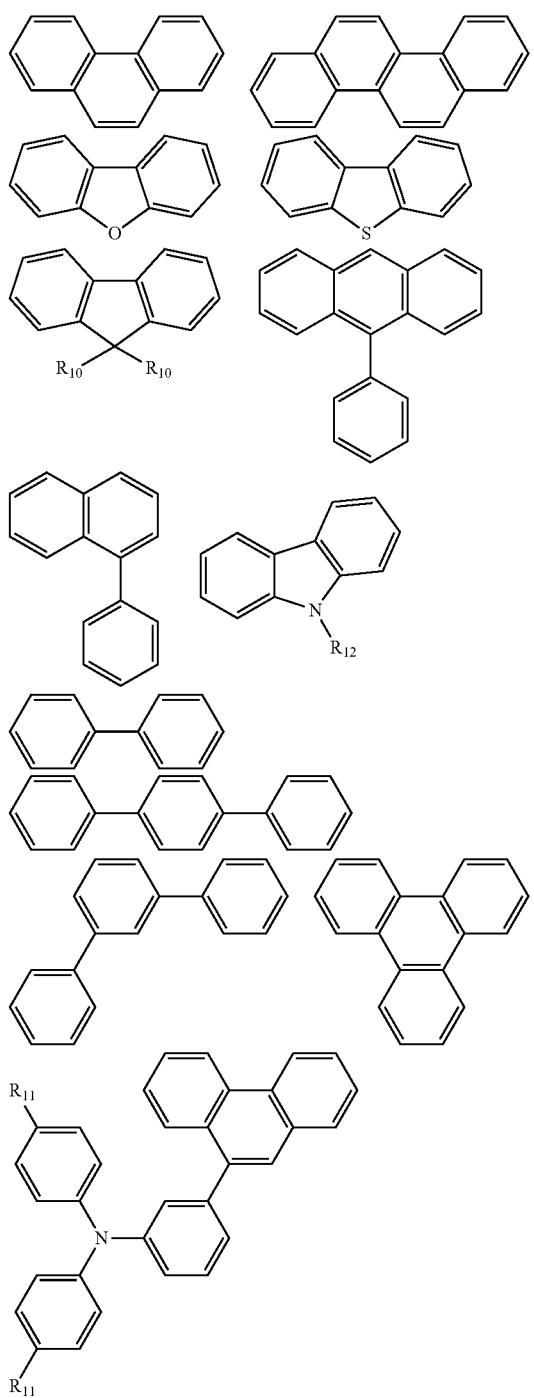

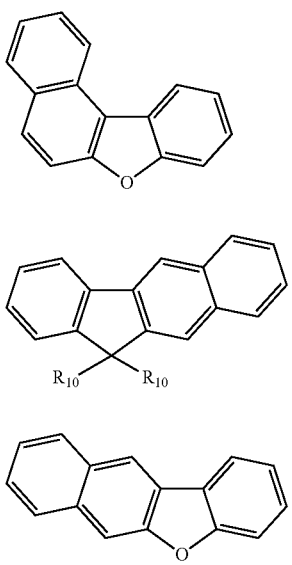

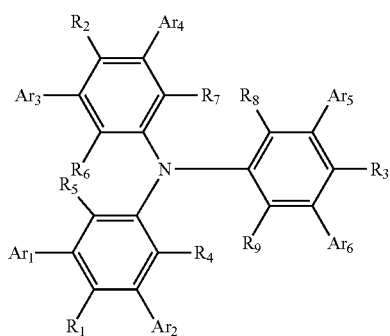

where each of $R_{10}$ and $R_{12}$ independently represents an alkyl group or an aryl group and represents an alkyl group, an alkenyl group, or an alkoxy group.

21. An electrochromic compound represented by formula (1):

Formula (1)

where each of $R_1$ to $R_9$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

each of $Ar_1$ to $Ar_6$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

at least one of $Ar_1$ to $Ar_6$ represents an aryl group, a heteroaryl group, or a group selected from the group consisting of

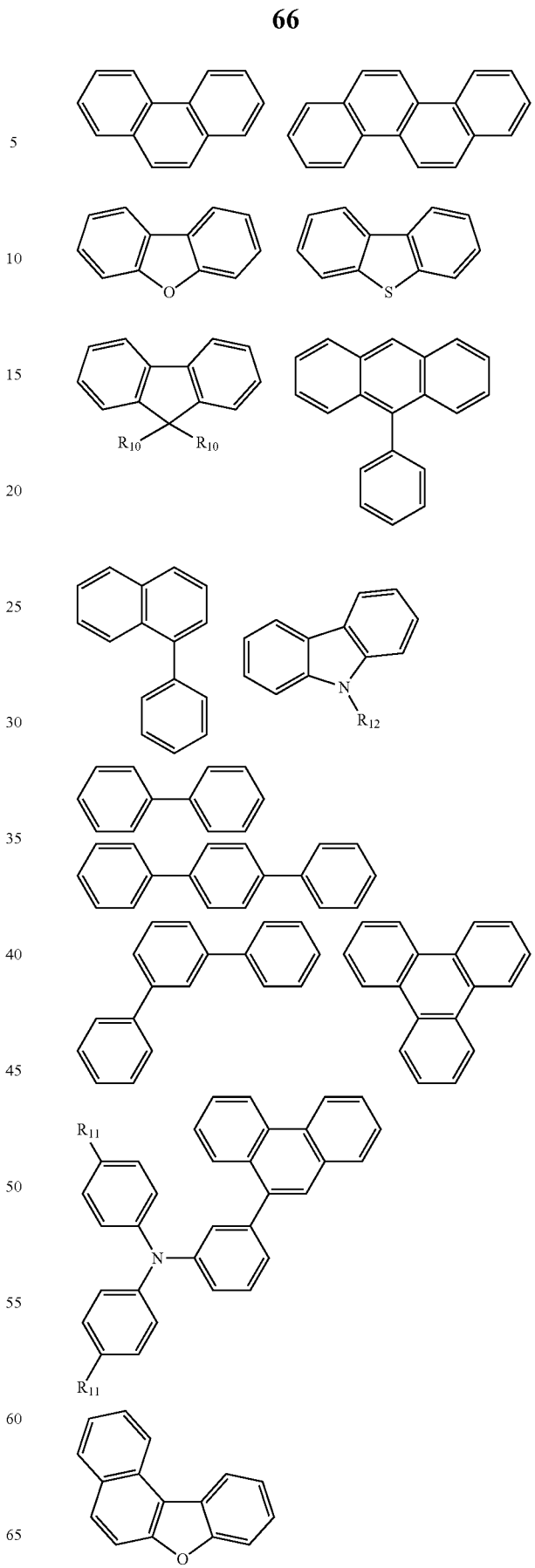

-continued

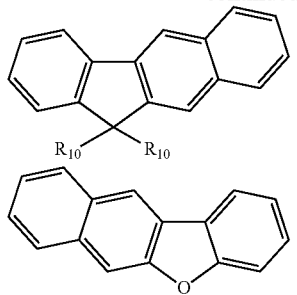
and

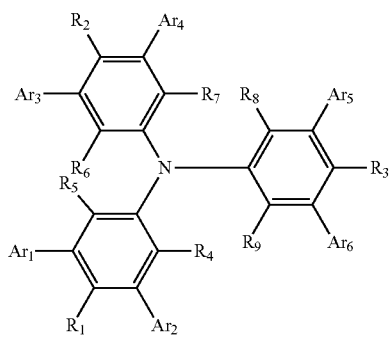

among Ar₁ to Ar₆, no more than one group attached to the same aryl group of the formula (1) is a group in which at least two aryl groups are condensed with each other to form a ring, and wherein among Ar₁ to Ar₆, no more than one group attached to the same aryl group of the formula (1) is a group in which two or more aryl and/or heteroaryl groups are bound to each other via a covalent bond.

22. An electrochromic compound represented by formula (1):

Formula (1)

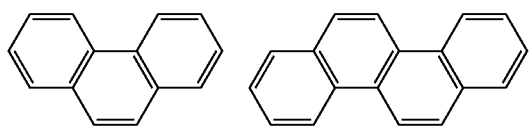

where each of $R_1$ to $R_9$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

each of Ar₁ to Ar₆ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

at least one of Ar₁ to Ar₆ represents an aryl group, a heteroaryl group, or a group selected from the group consisting of -continued

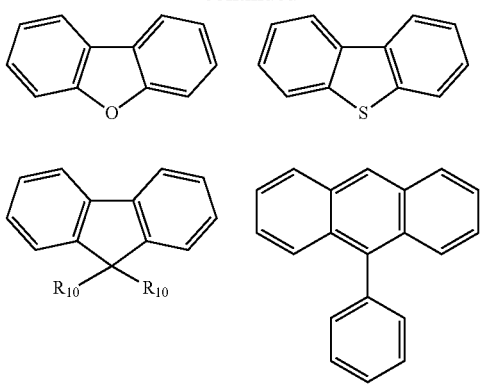

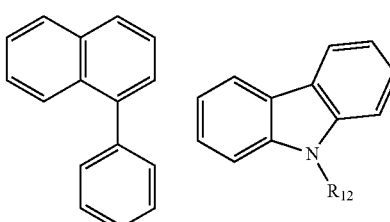

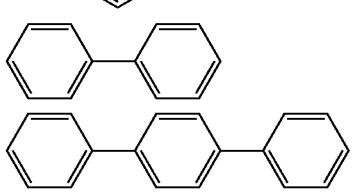

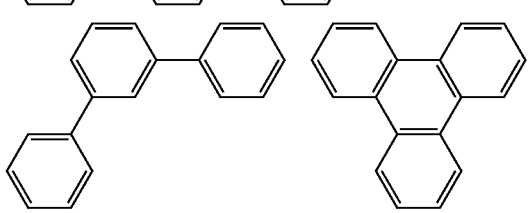

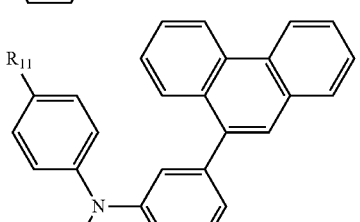

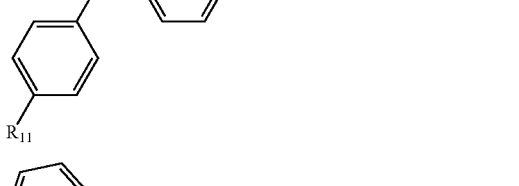

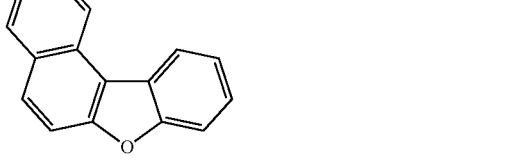

and

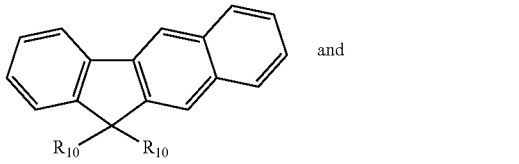

-continued

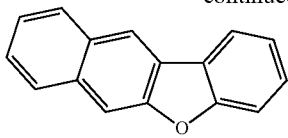

among Ar₁ to Ar₆, no more than one group attached to the same aryl group of the formula (1) is a group in which at least two aryl groups are condensed with each other to form a ring, and among Ar₁ to Ar₆, no more than one group attached to the same aryl group of the formula (1) is a group in which at least two heteroaryl groups are condensed with each other to form a ring.

23. An electrochromic composition, comprising:
an electrochromic compound; and
a radical polymerizable compound,
wherein the electrochromic compound is represented by formula (1):

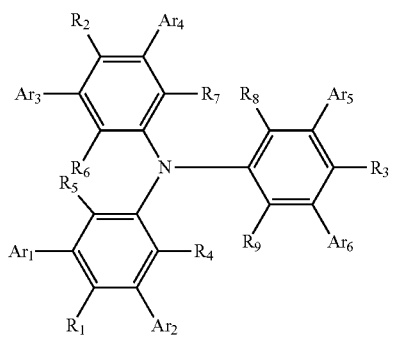

Formula (1)

where each of $R_1$ to $R_9$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

each of $Ar_1$ to $Ar_6$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

at least one of $Ar_1$ to $Ar_6$ represents an aryl group, a heteroaryl group, or a group selected from the group consisting of

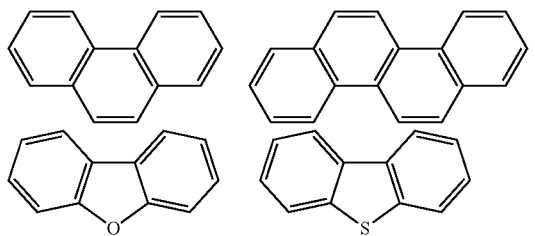

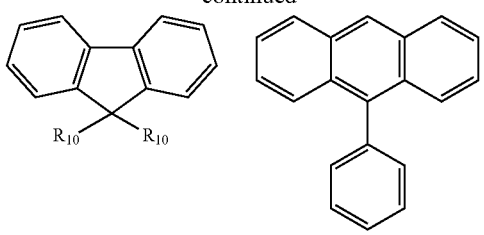

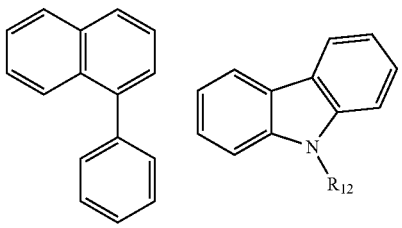

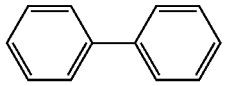

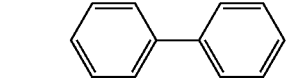

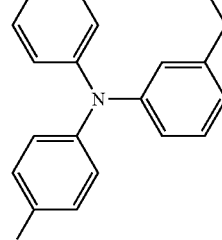

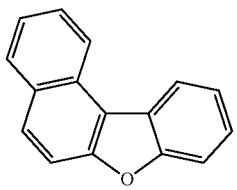

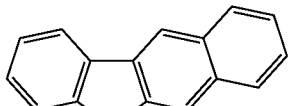 and

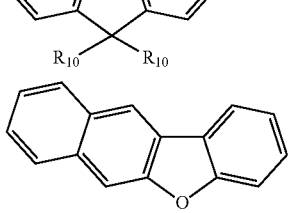

among Ar₁ to Ar₆, no more than one group attached to the same aryl group of the formula (I) is a group in which at least, two aryl groups are condensed with each other to form a ring.

24. An electrochromic element, comprising:
   a first electrode;
   an electrochromic layer on the first electrode, the electrochromic layer containing an electrochromic compound;
   a second electrode facing the first electrode with a gap therebetween; and
   an electrolyte layer disposed between the first electrode and the second electrode,
   wherein the electrochromic compound is represented by formula (1):

Formula (1)

where each of $R_1$ to $R_9$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

each of $Ar_1$ to $Ar_6$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

at least one of $Ar_1$ to $Ar_6$ represents an aryl group, a heteroaryl group, or a group selected from the group consisting of -continued and among $Ar_1$ to $Ar_6$, no more than one group attached to the same aryl group of the formula (1) is a group in which at least two aryl groups are condensed with each other to form a ring.

25. An electrochromic element, comprising:
a first electrode;
a second electrode facing the first electrode with a gap therebetween; and
an electrolyte layer disposed between the first electrode and the second electrode, the electrolyte layer containing an electrochromic compound represented by formula (1):

Formula (1)

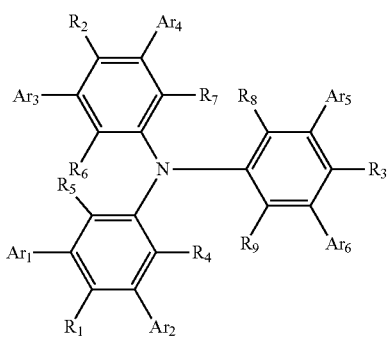

where each of $R_1$ to $R_9$ independently represents one selected from the group consisting of a hydrogen atom, a halogen atom, a monovalent organic group, a group in which two or more awl and/or heteroaryl groups are bound to each other via a covalent bond, a group in which two or more aryl and/or heteroaryl groups are condensed with each other to form a ring, and a polymerizable functional group;

each of $Ar_1$ to $Ar_6$ independently represents one selected from the group consisting of a hydrogen atom, a halogen atom, a monovalent organic group, a group in which two or more aryl and/or heteroaryl groups are bound to each other via a covalent bond, a group in which two or more aryl and/or heteroaryl groups are condensed with each other to form a ring, and a polymerizable functional group;

at least one of $Ar_1$ to $Ar_6$ represents an aryl group, a heteroaryl group, or a group selected from the group consisting of

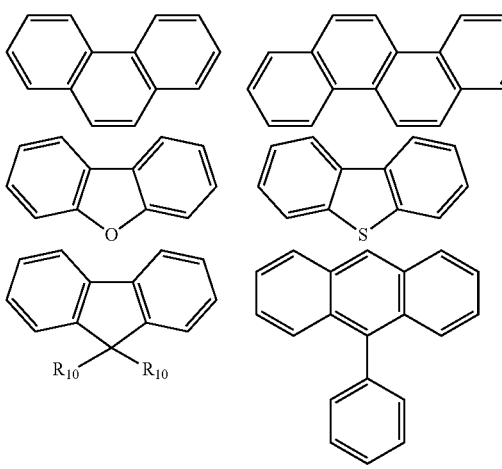

-continued

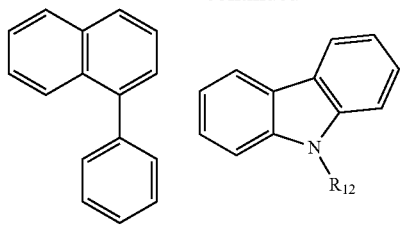

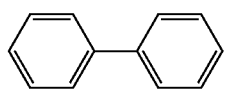

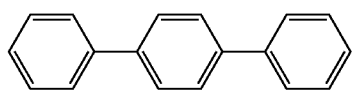

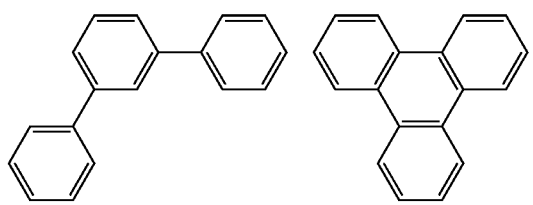

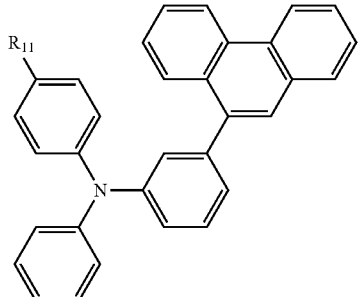

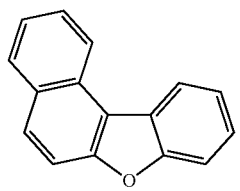

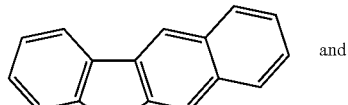

and

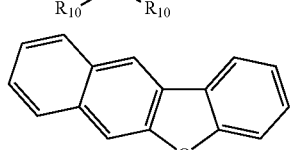

among $Ar_1$ to $Ar_6$, no more than one group attached to the same aryl group of the formula (1) is a group in which at least two aryl groups are condensed with each other to form a ring.

* * * * *